US009803006B2

(12) United States Patent
Zhou et al.

(10) Patent No.: US 9,803,006 B2
(45) Date of Patent: *Oct. 31, 2017

(54) TARGETING OF HERPES SIMPLEX VIRUS TO SPECIFIC RECEPTORS

(71) Applicant: THE UNIVERSITY OF CHICAGO, Chicago, IL (US)

(72) Inventors: Guoying Zhou, Madison, WI (US); Bernard Roizman, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 76 days.

This patent is subject to a terminal disclaimer.

(21) Appl. No.: 14/589,581

(22) Filed: Jan. 5, 2015

(65) Prior Publication Data

US 2016/0175370 A1  Jun. 23, 2016

Related U.S. Application Data

(63) Continuation of application No. 12/065,455, filed as application No. PCT/US2006/033865 on Aug. 30, 2006, now Pat. No. 8,927,251, which is a continuation of application No. 11/215,636, filed on Aug. 30, 2005, now Pat. No. 7,550,148, which is a continuation-in-part of application No. 10/530,774, filed as application No. PCT/US03/31598 on Oct. 6, 2003, now Pat. No. 7,501,126.

(60) Provisional application No. 60/416,716, filed on Oct. 7, 2002.

(51) Int. Cl.

| | |
|---|---|
| C07K 14/00 | (2006.01) |
| C07K 16/18 | (2006.01) |
| A61K 47/48 | (2006.01) |
| C07K 14/54 | (2006.01) |
| A61K 38/20 | (2006.01) |
| C12N 15/869 | (2006.01) |
| C12N 15/86 | (2006.01) |
| C12Q 1/70 | (2006.01) |
| A61K 35/00 | (2006.01) |

(52) U.S. Cl.
CPC .......... *C07K 16/18* (2013.01); *A61K 38/2086* (2013.01); *A61K 47/48269* (2013.01); *A61K 47/48376* (2013.01); *A61K 47/48776* (2013.01); *C07K 14/5437* (2013.01); *C12N 15/86* (2013.01); *C12N 15/8695* (2013.01); *A61K 35/00* (2013.01); *C12N 2710/16632* (2013.01); *C12N 2710/16643* (2013.01); *C12N 2710/16645* (2013.01); *C12N 2799/028* (2013.01); *C12N 2810/50* (2013.01); *C12N 2810/852* (2013.01); *C12Q 1/705* (2013.01)

(58) Field of Classification Search
None
See application file for complete search history.

(56) References Cited

U.S. PATENT DOCUMENTS

| | | | |
|---|---|---|---|
| 5,599,691 A | 2/1997 | Roizman | |
| 7,501,126 B2* | 3/2009 | Roizman | A61K 47/48269 424/199.1 |
| 7,550,148 B2* | 6/2009 | Zhou | A61K 47/48269 424/199.1 |
| 8,927,251 B2* | 1/2015 | Zhou | C12N 15/86 424/199.1 |

FOREIGN PATENT DOCUMENTS

| | | |
|---|---|---|
| WO | WO-99/06583 | 2/1999 |
| WO | WO-2004/033639 | 4/2004 |

OTHER PUBLICATIONS

Zhou and Roizman. Construction and properties of a herpes simplex virus 1 designed to enter cells solely via the IL-13alpha2 receptor. Proc Natl Acad Sci U S A. Apr. 4, 2006;103(14):5508-13.*
Arsenakis et al., Expression and regulation of glycoprotein C gene of herpes simplex virus 1 resident in a clonal L-cell line,. *J. Virol.*, 58(2):367-76 (1986).
Brooks et al., Integrin alpha v beta 3 antagonists promote tumor regression by inducing apoptosis of angiogenic blood vessels, *Cell*, 79:1157-64 (1994).
Brooks et al., Requirement of vascular integrin alpha v beta 3 for angiogenesis, *Science*, 264:569-71 (1994).
Brunetti et al., Herpes simplex virus gD and virions accumulate in endosomes by mannose 6-phosphate-dependent and -independent mechanisms, *J. of Virol.*, 72(4):3330-9 (1998).
Burger, et al., Expression analysis of delta-catenin and prostate-specific membrane antigen: their potential as diagnostic markers for prostate cancer, *Int. J. Cancer*, 100:228-37 (2002).
Campadelli-Fiume, et al., The novel receptors that mediate the entry of herpes simplex viruses and animal alphaherpesviruses into cells, *Rev. Med.l Virol.*, 10:305-319 (2000).

(Continued)

*Primary Examiner* — Michelle S Horning
(74) *Attorney, Agent, or Firm* — Marshall, Gerstein & Borun LLP

(57) ABSTRACT

The invention relates to engineered Herpes simplex virus (HSV) particles that are targeted to one or more specific binding pair members, such as receptors. Also, recombinant vectors for producing such HSV particles are provided. By reducing the affinity of HSV for its natural receptor(s) and increasing the affinity for a selected receptor, the HSV particles of the invention are useful for targeting cells that express the selected receptor, which itself may be a product of genetic engineering. The ability to selectively target cells renders the HSV particles, particularly useful in selectively diagnosing, treating, and imaging cells bearing the selected binding pair member, such as a receptor. The invention also provides for polynucleotide-based therapy to cells bearing the selected binding pair member such as a receptor.

6 Claims, 7 Drawing Sheets

(56) References Cited

OTHER PUBLICATIONS

Carfi, et al., Herpes simplex virus glycoprotein D bound to the human receptor HveA, *Mol. Cell.*, 8(1):169-79 (2001).
Cassady, et al., The second-site mutation in the herpes simplex virus recombinants lacking the gamma134.5 genes precludes shutoff of protein synthesis by blocking the phosphorylation of elF-2alpha, *J. Virol.*, 72(9):7005-11 (1998).
Chou et al., Association of a M(r) 90,000 phosphoprotein with protein kinase PKR in cells exhibiting enhanced phosphorylation of translation initiation factor elF-2 alpha and premature shutoff of protein synthesis after infection with gamma 134.5-mutants of herpes simplex virus 1, *Proc. Natl. Acad. Sci. USA*, 92(23):10516-20 (1995).
Cocchi et al., The ectodomain of a novel member of the immunoglobulin subfamily related to the poliovirus receptor has the attributes of a bona fide receptor for herpes simplex virus types 1 and 2 in human cells, *J. Virol.*, 72:9992-10002 (1998).
Connolly et al., Structure-based mutagenesis of herpes simplex virus glycoprotein D defines three critical regions at the gD-HveA/HVEM binding interface, *J. Virol.*, 77:8127-40 (2003).
Connolly et al., Potential nectin-1 binding site on herpes simplex virus glycoprotein d, *J. Virol.*, 79:1282-95 (2005).
Davis, et al., Survival rates in patients with primary malignant brain tumors stratified by patient age and tumor histological type: an analysis based on Surveillance, Epidemiology, and End Results (SEER) data, 1973-1991, *J. Neurosurg.*, 88:1-10 (1998).
Debinski et al., Receptor for interleukin 13 is a marker and therapeutic target for human high-grade gliomas, *Clin. Can. Res.*, 5:985-90 (1999).
Debinski, An immune regulatory cytokine receptor and glioblastoma multiforme: an unexpected link, *Crit. Rev. Oncogen*, 9:255-68 (1998).
Debinski et al., Retargeting interleukin 13 for radioimmunodetection and radioimmunotherapy of human high-grade gliomas, *Clin. Cancer Res.*, 5(10 Suppl):3143s-7s (1999).
Debinski et al., Molecular expression analysis of restrictive receptor for interleukin 13, a brain tumor-associated cancer/testis antigen, *Mol. Med.*, 6:440-49 (2000).
Ellerman et al., Identification of a determinant of epidermal growth factor receptor ligand-binding specificity using a truncated, high-affinity form of the ectodomain, *Biochemistry*, 40:8930-9 (2001).
Fracasso et al., Anti-tumor effects of toxins targeted to the prostate specific membrane antigen, *Prostate*, 53:9-23 (2002).
Gembitsky et al., A specific binding site for a fragment of the B-loop of epidermal growth factor and related peptides, *Peptides*. 23:97-102 (2002).
Hayashi et al., MUC1 mucin core protein binds to the domain 1 of ICAM-1, *Digestion*, 63:87-92 (2001).
He et al., Suppression of the phenotype of gamma(1)34.5-herpes simplex virus 1: failure of activated RNA-dependent protein kinase to shut off protein synthesis is associated with a deletion in the domain of the alpha47 gene, *J. Virol.*, 71(8):6049-54 (1997).
International Preliminary Report on Patentability for corresponding PCT/US06/033865, dated Mar. 4, 2008.
International Preliminary Report on Patentability, PCT/US2006/032291, dated Feb. 13, 2007.
International Search Report and Written Opinion, PCT/US2006/033865, dated Jan. 24, 2007.
International Search Report, PCT/US2006/032291, dated Feb. 13, 2007.
Laquerre et al., Heparan sulfate proteoglycan binding by herpes simplex virus type 1 glycoproteins B and C, which differ in their contributions to virus attachment, penetration, and cell-to-cell spread, *J. Virol.*, 72(7):6119-30 (1998).
Leib, et al., Interferons regulate the phenotype of wild-type and mutant herpes simplex viruses in vivo, *J. Exp. Med.*, 189:663-72 (1999).
Lorimer et al., Targeting retrovirus to cancer cells expressing a mutant EGF receptor by insertion of a single chain antibody variable domain in the envelope glycoprotein receptor binding lobe, *J Immunol Methods*, 237(1-2):147-57 (2000).
Mabjeesh et al., Gene therapy of prostate cancer: current and future directions, *Endo. Related Cancer*, 9:115-39 (2002).
Manoj et al., Mutations in herpes simplex virus glycoprotein D that prevent cell entry via nectins and alter cell tropism, *Pro. Nat. Acad. Sci. USA*, 101:12414-21 (2004).
Markert et al., Conditionally replicating herpes simplex virus mutant, G207 for the treatment of malignant glioma: results of a phase I trial, *Gene Ther.*, 7(10):867-74 (2000).
McKie, et al., Histopathological responses in the CNS following inoculation with a non-neurovirulent mutant (1716) of herpes simplex virus type 1 (HSV 1): relevance for gene and cancer therapy, *Neuropathol Appl Neurobiol.*, 24(5):367-72 (1998).
Milne et al., Function of herpes simplex virus type 1 gD mutants with different receptor-binding in affinities in virus entry and fusion, *J. Virol.*, 77:8962-72 (2003).
Mineta et al., Attenuated multi-mutated herpes simplex virus-1 for the treatment of malignant gliomas, *Nat Med.*, 1(9):938-43 (1995).
Mintz A., et al., IL-13Ralpha2 is a glioma-restricted receptor for interleukin-13, *Neoplasia*, 4:388-99 (2002).
Montgomery, et al., Herpesvirus entry mediator, a member of the tumor necrosis factor receptor (TNFR) family, interacts with members of the TNFR-associated factor family and activates the transcription factors NF-kappaB and AP-1, *Cell*, 87:427-436 (1996).
Pyles, et al., A novel multiply-mutated HSV-1 strain for the treatment of human brain tumors, *Hum Gene Ther.*, 8(5):533-44 (1997).
Rampling et al., Toxicity evaluation of replication-competent herpes simplex virus (ICP 34.5 null mutant 1716) in patients with recurrent malignant glioma, *Gene Ther.*, 7(10):859-66 (2000).
Ross, et al., Prostate stem cell antigen as therapy target: tissue expression and in vivo efficacy of an immunoconjugate, *Cancer Res.* 62:2546-2553 (2002).
Ruoslahti, E., RGD and other recognition sequences for integrins, *Anu. Rev. Cell Dev. Biol.* 12:697-715 (1996).
Sharma, et al., Molecular imaging of gene expression and protein function in vivo with PET and SPECT, *J Magn Reson Imaging*, 16(4):336-51 (2002).
Shin et al., Formation of polyomavirus-like particles with different VP1 molecules that bind the urokinase plasminogen activator receptor, *J. Virol.*, 77: 11491-8 (2003).
Simard et al., Sequence analysis of the UL39, UL38, and UL37 homologues of bovine herpesvirus 1 and expression studies of UL40 and UL39, the subunits of ribonucleotide reductase, *Virology*, 212(2):734-40 (1995).
Soling et al., Intracellular localization of Herpes simplex virus type 1 thymidine kinase fused to different fluorescent proteins depends on choice of fluorescent tag, *FEBS Lett.*, 527(1-3):153 (2002).
Spear et al., Three classes of cell surface receptors for alphaherpesvirus entry, *Virology*, 275:1-9 (2000).
Thomas et al., Preoperative combined nested reverse transcriptase polymerase chain reaction for prostate-specific antigen and prostate-specific membrane antigen does not correlate with pathologic stage or biochemical failure in patients with localized prostate cancer undergoing radical prostatectomy, *J. Clin. Oncol.*, 20:3213-18 (2002).
Turner et al., Glycoproteins gB, gD, and gHgL of herpes simplex virus type 1 are necessary and sufficient to mediate membrane fusion in a Cos cell transfection system, *J. Virol.*, 72(1): 873-75 (1998).
Urbanelli et al., Targeted gene transduction of mammalian cells expressing the HER2/neu receptor by filamentous phage, *J. Mol. Biol.*, 313(5):965-76 (2001).
VanBeusechem et al., Efficient and selective gene transfer into primary human brain tumors by using single-chain antibody-targeted adenoviral vectors with native tropism abolished, *J. Virol.*, 76:2753-62 (2002).
Vries et al., Positron Emission Tomography: Measurement of Transgene Expression, *Methods*, 27(3): 234 (2002).
De Vries et al., Scintigraphic imaging of HSVtk gene therapy, *Curr. Pharm. Des.*, 8(16):1435-50 (2002).

(56) References Cited

OTHER PUBLICATIONS

Ye et al., The essential protein encoded by the UL31 gene of herpes simplex virus 1 depends for its stability on the presence of UL34 protein, *Proc. Natl. Acad. Sci. USA*, 97(20):11002-7 (2000).

Yoon et al., Mutations in the N termini of herpes simplex virus type 1 and 2 gDs alter functional interactions with the entry/fusion receptors HVEM, nectin-2, and 3-O-sulfated heparan sulfate but not with nectin-1, *J. Virol.*, 9221-31 (2003).

Zago et al., Use of herpes simplex virus and pseudorabies virus chimeric glycoprotein D molecules to identify regions critical for membrane fusion, *Proc. Natl. Acad. Sci. USA.*, 101: 17498-03 (2004).

Zhou et al., Characterization of a recombinant herpes simplex virus 1 designed to enter cells via the IL13R alpha 2 receptor of malignant glioma cells, *J. Virol.*, 79:5272-7 (2005).

Zhou et al., Engineered herpes simplex virus 1 is dependent on IL13Ralpha 2 receptor for cell entry and independent of gylcoprotein D receptor interaction, *Proc. Nat. Acad. Sci. USA*, 99: 15124-9 (2002).

Zhou et al., The essential protein encoded by the UL31 gene of herpes simplex virus 1 depends for its stability on the presence of UL34 protein, *Proc. Natl. Acad. Sci. USA*, 103:5508-13 (2006).

Zhou et al., Glycoprotein D or J delivered in trans blocks apoptosis in SK—N—SH cells induced by a herpes simplex virus 1 mutant lacking intact genes expressing both glycoproteins, *J. Virol.*, 74(24):11782-91 (2000).

Zhou et al., The domains of glycoprotein D required to block apoptosis depend on whether glycoprotein D is present in the virions carrying herpes simplex virus 1 genome lacking the gene encoding the glycoprotein, *J. Virol.*, 75(13):6166-72 (2001).

Zhou et al., Cation-independent mannose 6-phosphate receptor blocks apoptosis induced by herpes simplex virus 1 mutants lacking glycoprotein D and is likely the target of antiapoptotic activity of the glycoprotein, *J. Virol.*, 76(12):6197-204 (2002).

\* cited by examiner

The amino terminal sequence of IL13-gC

```
cttggtcgggaggcccgcatcgaacgcacaccccatccggtggtccgtgtggaggtcgttttcagtgcc
ggtctcgctttgccggg**cgtaAggctcATGGCGCTTTTGTTGACCACGGTCATTGCTCTCACTTGCC
     gC upstream           |        |--> IL-13*
GGCGGCTTTGCCTCCCCAGGCCCTGTGCCTCCCTCTACAGCCCTCAGGAGCTCATTGAGGAGCTGGTCA
ACATCACCCAGAACCAGAAGGCTCCGCTCTGCAATGGCAGCATGGTATGGAGCATCAACCTGACAGCTG
GCATGTACTGTGCAGCCCTGGAATCCCTGATCAACGTGTCAGGCTGCAGTGCCATCGAGAAGACCCAGA
GGATGCTGAGCGGATTCTGCCCGCACAAGGTCTCAGCTGGGCAGTTTTCAGCTTGCATGTCCGAGACAC
CAAAACGAGGTGGCCCAGTTTGTAAAGATCTGCTCTTACATTTAAAGAAACTTTTTCGCGAGGGACGGT
Tgaat*
GCACCCCGCATGGAGTTCCGCCTCCAGATATGGCGTTACTCCATGGGTCCGTCCCCCCCAATCGCTCCGGC
        |--> gc downstream
```

FIG. 2A

The sequence of the gB$_{\Delta poly(K)}$ domain

```
GCGTCCTGGTGGCCGTCGGCGGCTTCGAAGTTCCTCCCGGCACGCCTGGGGTCGCGGCCGCGACCCAGGCGGC
GAACGGGGGACCTGCCACTCGGCCGCCGCCCGCCCCGCGCCCGCCCAACCGGGGATCCGAAACCGAAG
AGAACAGAAAACCGAAACCGCCCAAAGCGCCGCCGCCCCGCCGGCGACAACGCCGACCGTCGCCGCGGCCA
CGCCACCGTGCCCGAGCACCTGCGGGACATCAAGGCGGAGAACACCGATGCAAACTTTTACGTGTGCCCA
CCCCCACGGGCGCCACGGTGGTGCAGTTCGAGCAGCCCGCGCCGCTCCCCTACCCCGGCCCGAGGGTCAGA
```

FIG. 2B

The amino terminal sequence of IL13-gD

```
ATGGGGGGGCTGCCGCCAGGTTGGGGGCCCGTGATTTTGTTTGTCGTCATAGTCGGCCTC
Signal peptide of gD-->
CATGGGGTCCGCGGCAAATATGCCTTGGCGGATGCCTCTCTCAAGCTGGCCGACCCCAAT
                     |--
CGCTTTCGCCGCAAGACCTTCCGGTCctcgag*ATGGCGCTTTTGTTGACCACGGTCATT
                        24AA XhoI  IL13-->
GCTCTCACTTGCCTTGGCGGCTTTGCCTCCCCAGGCCCTGTGCCTCCCTCTACAGCCCTC
AGGGAGCTCATTGAGGAGCTGGTCAACATCACCCAGAACCAGAAGGCTCCGCTCTGCAAT
GGCAGCATGGTTTGGAGCATCAACCTGACAGCTGGCATGTACTGTGCAGCCCTGGAATCC
CTGATCAACGTGTCAGGCTGCAGTGCCATCGAGAAGACCCAGAGGATGCTGAGCGGATTC
TGCCCGCACAAGGTCTCAGCTGGGCAGTTTTCAGCTTGCATGTCCGAGACACCAAAATC
GAGGTGGCCCAGTTTGTAAAGGACCTGCTCTTACATTTAAAGAAACTTTTTCGCGAGGGA
CGGTTCAACTGAAAC*ggtaccCTGGACCAGCTGACCGACCCTCCGGGGTCCGGCGCTG
    <--IL13 KpnI 75AA
TACCACATCCAGGCGGGCCTACCGGACCCGTTCCAGCCCCCAGCCTCCCGATC
```

FIG. 2C pgD- in pcDNA3.1(-) with CMV promoter collapsed by NruI/NheI digestion. The fragment containing gD upstream at NotI/BamHI, and gD downstream at XhoI/KpnI in pBluescript II SK was excised by NotI/KpnI and ligated into pcDNA3.1(-) in which the CMV promoter had been collapsed. N, NotI, B, BamHI, P, PstI, E, EcoRI, H, HindIII, C, ClaI, X, XhoI, and K, KpnI.

TARGETING OF HERPES SIMPLEX VIRUS TO SPECIFIC RECEPTORS

This application is a continuation-in-part application of U.S. Ser. No. 10/530,774, which is the US national phase of PCT/US03/31598 filed Oct. 6, 2003, which claims the priority benefit of U.S. Ser. No. 60/416,716, filed Oct. 7, 2002.

GOVERNMENT INTERESTS

The U.S. Government owns rights in the invention pursuant to National Cancer Institute grant number 1PO1 CA71933.

BACKGROUND OF THE INVENTION

A steady rate of healthcare advances has led to continuing improvement in the health and quality of life for humans and animals. Nevertheless, a variety of diseases, disorders, and conditions have largely eluded the best efforts at prevention or treatment. Chief among these maladies is the loss of cell-cycle control that frequently results in the undesirable cell proliferation characteristic of cancer in its many forms, such as malignant glioma. Malignant gliomas are devastating brain tumors that afflict animals such as humans. The average life span after diagnosis is less than one year and few patients have been reported to survive five years. Furthermore, none of the conventional anti-cancer therapies has been successful in significantly prolonging the lifespan of patients with this disease. In recent years there have been numerous attempts to use genetically engineered herpes simplex viruses (HSV) as oncolytic agents to treat malignant gliomas. Because wild-type viruses are highly virulent, the viruses used in preclinical evaluations and in phase-1 clinical studies have been thoroughly attenuated. While several deletion mutants have been tested, the mutants that reached clinical trials lacked the $\gamma_1 34.5$ gene encoding infected cell protein 34.5 (ICP34.5) and optionally, the $U_L 39$ gene encoding the large subunit of ribonucleotide reductase.

These attenuated HSV viruses, however, have been imperfectly engineered as oncolytic agents. One advantage of these mutant viruses is that they have a significantly reduced capacity to replicate in normal, non-dividing cells in vivo. Viral ribonucleotide reductase is an essential gene for viral replication in resting cells and, hence, the $U_L 39$ mutant virus is dysfunctional in the normal environment of the central nervous system (Simard et al. 1995). The major function of ICP34.5 is to preclude the shutoff of protein synthesis caused by activation of protein kinase R in infected cells. Once activated, this enzyme phosphorylates the a subunit of translation initiation factor 2 (eIF2α), resulting in complete cessation of translation. Mutants lacking the $\gamma_1 34.5$ genes are highly attenuated because the lytic life cycle is completely blocked in an interferon+ cellular background. In contrast, $\gamma_1 34.5$ mutants are nearly as virulent as wild-type virus in mice lacking interferon receptor. Although mutants deleted in both $\gamma_1 34.5$ and $U_L 39$ are not significantly more attenuated than those lacking the $\gamma_1 34.5$ genes, such mutants do provide added insurance in the form of a reduced risk of reversion.

A significant disadvantage of these mutant HSV viruses is their poor replication, even in dividing cells. In experimental animal systems, the mutant viruses do not exhibit sustained lytic life cycles, with the loss of a potentially amplified response to a given therapeutic dose of the virus that would be expected upon re-infection of tumor cells by the multiplied viral progeny. Consequently, maximum killing of tumors cells requires high doses of virus. Given the poor growth of these mutant HSV viruses, even in dividing cells, production of virus pools large enough to yield efficacious inocula of >$10^9$ plaque forming units (PFU) has remained a major obstacle. Moreover, indiscriminate binding of virus to non-tumor cells further diminishes the effectiveness of HSV virus dosages because mis-targeted viral particles do not contribute to the desired beneficial therapeutic effect of tumor cell destruction. One approach to overcoming these obstacles is to achieve a more thorough understanding of the HSV lytic life cycle and thereby facilitate the development of HSV mutants tailored for use as targeted therapeutic agents, such as targeted oncolytic agents.

HSV enters host cells using a two-step mechanism. The first step of entry is HSV attachment to the cell surface. This step is initiated by glycoproteins B and C (gB and gC), which project from the viral envelope, attaching to heparan sulfate proteoglycans on host cell surfaces. The gB and gC domains interacting with heparan sulfate have been mapped at the sequence level (Laquerre et al. 1998). Following this initial attachment, viral glycoprotein D (gD) interacts with one of several receptors. Of these gD receptors, two are particularly important for entry (Spear et al, 2000). One receptor, designated HveA (formerly, HveM), is a member of the family of receptors for tumor necrosis proteins. A second receptor, designated Nectin-1 (HveC), is a member of the nectin family of proteins, structurally related to the immunoglobulin superfamily, which serve as intercellular connectors (Campadelli-Fiume et al. 2000). The second step of HSV entry into a cell is fusion of the viral envelope with the plasma membrane of the cell. To effect fusion, gD, when bound to its receptor, recruits glycoproteins B, H and L, which results in fusion of the envelope with the plasma membrane.

Additional understanding of HSV infection has come from recent studies that have lent significance to an old observation that gD interacts with the cation-independent mannose 6 phosphate receptor, contributing to the accumulation of HSV in endosomes. Endocytosis of viral particles results in particle degradation by lysosomal enzymes, but the cells succumb as a consequence of the degradation of cellular DNA by lysosomal DNase. HSV gD blocks this apoptotic pathway to cell death through its interaction with the mannose 6 phosphate receptor. Thus, gD interacts with HveA, nectins, the mannose 6 phosphate receptor, and at least one of the complex of viral glycoproteins involved in the fusion of HSV with the plasma membrane.

In an attempt to target HSV-1 infection to specific cells, a recombinant HSV having a chimeric protein comprising gC and erythropoietin (EPO) on its surface was constructed. Although the recombinant virus bound to cells expressing EPO receptor and endocytosis of the virus occurred, successful infection of these EPO-receptor expressing cells did not occur.

Accordingly, a need continues to exist in the art for viral therapeutic agents exhibiting improved targeting capacities while retaining sufficient capacity to infect to be therapeutically useful. Ideally, suitable viruses would be therapeutic agents, such as oncolytic agents, themselves as well as providing a targeting vehicle or vector for the controlled delivery of polynucleotide coding regions useful as therapeutic agents. Another need in the art is for targeted agents useful in diagnostic applications as, e.g., imaging agents or targeted vehicles for imaging agents.

SUMMARY

The invention satisfies the aforementioned need in the art by providing viral forms suitable for use as therapeutic and diagnostic agents themselves, as well as providing a ready vehicle for the delivery of therapeutic or diagnostic polynucleotide coding regions to cells. These viral forms are modified viruses of the Herpesviridae family of viruses, and are preferably derived from herpes simplex virus type 1 or type 2. The invention provides a method of making virus particles with a novel ligand (or binding pair member), and making said particles totally dependent on a receptor of the ligand (or binding pair member) for entry into targeted cells.

Disclosed herein are methods to modify the surface of, e.g., an HSV virus particle in a manner that targets the virus to a specific receptor present on the surface of a cell of choice, typically a cell in need of therapy or a cell whose presence provides information of diagnostic value. The invention provides viral particles, e.g., HSV particles, having a reduced affinity for their natural cell-surface receptor(s), and methods for producing and using such particles, which minimizes or eliminates the problem of reduced efficiency associated with the mis-targeting of therapeutic and diagnostic viruses. Additionally, the invention provides viral particles, e.g., HSV particles, that exhibit specific affinity for a cell surface component that is not a natural viral receptor and that is present solely or predominantly on a given target cell, as well as methods for producing and using such viruses. Modified viral particles (e.g., HSV) having increased affinity for a cell surface component associated with one or more target cells exhibit improved targeting capabilities relative to known viral particles. The modified HSV particles have reduced indiscriminate binding, thereby minimizing sequestration of viral dosages away from the target cells. The invention further provides modified viral particles, such as modified HSV particles, that have both a reduced affinity for natural viral receptors and an increased affinity for a cell surface component associated with a particular target cell(s), with the modified viral particle effectively recruiting that cell surface component for use as a viral receptor. Other benefits of the modified viruses are described herein and will be apparent to those of skill in the art upon review of this disclosure.

In one aspect, the invention provides a recombinant herpes simplex virus (HSV) particle having at least one protein on its surface, comprising: (a) an altered gD, wherein the alteration reduces binding of gD to one or more of its cellular receptors, said alteration comprising (i) a heterologous peptide ligand on the surface of the recombinant HSV particle forming a fusion protein with the altered gD; and (ii) an amino acid alteration; wherein said recombinant HSV particle preferentially binds to cells expressing a binding partner to said heterologous peptide ligand. In some embodiments, these particles preferentially bind to target cells (cell expressing a binding partner) in whole or part due to the greater frequency of the binding partner on the surface of the cell relative to any natural HSV binding proteins on the surface of that cell. In some embodiments, the recombinant HSV particle further comprises an altered viral surface protein, wherein the alteration reduces binding of the viral surface protein to a sulfated proteoglycan. Such recombinant herpes simplex virus (HSV) particles comprise a virus surface protein altered to reduce the wild-type level of binding of that protein to a sulfated proteoglycan on the surface of a cell and an altered gD. The altered gD exhibits a reduced binding to one or more of the natural cellular receptors for gD; the altered gD is also fused to a heterologous peptide ligand (or binding pair member) having a binding partner, e.g., a peptide ligand receptor, found on the surface of a cell. Stated in the alternative, this aspect of the invention provides a recombinant herpes simplex virus (HSV) particle having at least one protein on its surface, comprising: (a) an altered viral surface protein, wherein the alteration reduces binding of the viral surface protein to a sulfated proteoglycan; and (b) an altered gD, wherein the alteration reduces binding of gD to one or more of its cellular receptors, the alteration comprising (i) a heterologous peptide ligand (or binding pair member) on the surface of the recombinant HSV particle forming a fusion protein with the altered gD; and (ii) an amino acid alteration; wherein the recombinant HSV particle preferentially binds to cells expressing a binding partner to the heterologous peptide ligand (or binding pair member).

The invention comprehends a recombinant HSV particle wherein the amino acid alteration is selected from the group consisting of an amino acid deletion, an amino acid substitution and an amino acid insertion. A preferred site for the amino acid alteration is amino acid position 34 of gD. Exemplary recombinant HSV particles according to the invention include HSV R5141 and HSV R5161, each described below.

Contemplated amino acid alterations include insertions or deletions of 1-10 amino acids, such as insertions or deletions of 1-5 amino acids. Exemplary insertions occur immediately upstream (N-terminal) or downstream (C-terminal) to amino acid position 34 of gD. Exemplary deletions include amino acid position 34 of gD. For alterations comprising amino acid substitutions, 1-10 amino acids are substituted, such as substitutions of 1-5 amino acids. Non-contiguous (dispersed) or contiguous amino acid substitutions are contemplated. In some embodiments, conservative amino acids known in the art are substituted. Exemplary amino acid substitutions include single amino acid substitutions for the Serine at position 34 of gD. Preferably, substitutions for Ser34 will be conservative as, for example, an amino acid substitution of V34S in gD.

The altered gD, moreover, reduces binding of the recombinant HSV particle to at least one HSV entry mediator (Hve) cell-surface protein, such as an Hve selected from the group consisting of HveA (formerly, HveM) and Nectin-1 (HveC). Further, the recombinant HSV particles of the invention include particles wherein the altered viral surface protein is selected from the group consisting of gB and gC. In some embodiments, the altered viral surface protein, preferably selected from the group of gB and gC, forms a fusion protein with a heterologous peptide ligand. In some embodiments, the binding partner is a cell surface receptor for the heterologous peptide ligand.

The preferential binding of the recombinant HSV particles of the invention results in a detectable variation in effective binding of the particle to the cells being compared. By "effective binding" is meant either sufficiently stable binding to permit detection of binding or binding sufficient to result in productive infection of the cell. In preferred embodiments, the preferential binding is such that the recombinant HSV particles bind only to one of the cell types being compared (e.g., cancer cells compared to healthy cells of the same type). Suitable cells include any hyperproliferative cell type, such as a cancer cell. A cancer cell, in turn, includes a tumor cell, e.g., a malignant gliomal cell.

The invention comprehends recombinant HSV particles wherein the heterologous peptide ligand (or binding pair member) is any ligand (or binding pair member) for which a cell surface binding partner exists. Preferably, heterologous peptide ligands have specific cell surface binding partners, e.g., ligand receptors, that are preferentially exhibited on the surface of a target cell. More preferably, the cell surface binding partner is only exhibited on the surface of a target cell, when compared to the cells in an organism containing the target cell. Exemplary heterologous peptide ligands that include cytokines, such as IL13, and fragments, variants and derivatives thereof, provided that the ligand retains the capacity of binding to a cell-surface binding partner. An exemplary binding pair member contemplated as suitable for each aspect of the invention is a single-chain antibody, for which a binding partner would include an antigen thereof, or a fragment, derivative or variant thereof that retains the capacity to bind to the single-chain antibody.

Another aspect of the invention is drawn to the recombinant HSV particle described above, wherein a polynucleotide encoding the fusion protein is joined to a heterologous coding region for a leader sequence. In this context, "heterologous" means that the leader sequence is not found naturally associated with the upstream or 5' coding region participating in the fusion. Exemplary leader sequences include HSV leader sequences, e.g., an HSV gD leader sequence. In a related aspect, the invention provides the recombinant HSV particle described above, wherein a polynucleotide encoding the fusion protein is joined to a heterologous expression control element, such as a heterologous promoter (a promoter not naturally found in association with the polynucleotide coding region fused upstream or 5' in the fusion), a heterologous enhancer, or expression factor binding site known in the art.

Another aspect of the invention provides a pharmaceutical composition comprising a recombinant HSV particle described above and a pharmaceutically acceptable carrier, diluent, or excipient. Any pharmaceutical carrier, diluent or excipient known in the art is contemplated. A related aspect of the invention provides a kit comprising the pharmaceutical composition and a set of instructions for administering the composition to a subject in need. In each of these aspects of the invention, i.e., the pharmaceutical compositions and the kits, the heterologous peptide ligands (or binding pair members) and cell-surface binding partners described in the context of describing the recombinant HSV particles are contemplated.

Yet another aspect of the invention provides a method of targeting a recombinant HSV particle to a cell comprising (a) identifying a binding pair member, such as a ligand for a ligand binding partner, exhibited on the surface of a target cell; and (b) creating an HSV particle as described herein, wherein the ligand or, more generally, the binding pair member, binds to the binding partner exhibited on the surface of the target cell. In some preferred embodiments of this aspect of the invention, the altered viral surface protein is selected from the group consisting of gB and gC. In some embodiments, the alteration to gD reduces binding of gD to at least one cellular receptor for gD selected from the group consisting of HveA and Nectin-1. In preferred embodiments, the altered gD has a conservative substitution at position 34 of gD, such as a V34S substitution. A second fusion protein, joining the ligand (or binding pair member) and either of gB or gC, is also contemplated in some embodiments. Suitable cells for targeting include any hyperproliferative cell, such as a cancer cell, including tumor cells (e.g., malignant gliomal cells). Any of the heterologous peptide ligands (or binding pair members) and cell-surface binding partners described above in the context of describing the recombinant HSV particles is suitable for use in the method.

Another aspect of the invention is drawn to a method of imaging a cell comprising: (a) contacting the cell with a recombinant HSV particle as described above, the recombinant HSV particle further comprising a coding region for a marker protein; and (b) detecting the presence of the marker protein. Any type of cell exhibiting a cell-surface binding partner for a ligand (or binding pair member) fusible to HSV gD is suitable for use in this aspect of the invention, such as a cancer cell. Using cancer cells as an example, the method is useful provided that the binding partner is present at a higher number on the cancer cell as compared to a non-cancerous cell of the same type. Any known marker protein is useful in this aspect of the invention, e.g., a marker protein selected from the group consisting of thymidine kinase, green fluorescent protein, and luciferase. In preferred embodiments, the altered gD exhibits an amino acid substitution of V34S. Any of the heterologous peptide ligands (or binding pair members) and cell-surface binding partners described above in the context of describing the recombinant HSV particles is suitable for use in the method.

Another aspect of the invention provides a method of treating a cell-based disease comprising delivering a therapeutically effective amount of a recombinant HSV particle as described herein to a subject in need. A related aspect is the use of a recombinant HSV particle as described above in the preparation of a medicament for the treatment of a cell-based disease. A therapeutically effective amount of a recombinant HSV particle is that amount that produces the desired therapeutic effect, as would be understood and readily determinable by those of skill in the art. Any cell-based disease known or reasonably suspected to be amenable to treatment with a specifically targeted HSV is contemplated, e.g., a cell hyperproliferation disease such as cancer. Any of the heterologous peptide ligands (or binding pair members) and cell-surface binding partners described above in the context of describing the recombinant HSV particles is suitable for use in the method.

In a related aspect, the invention provides a method of ameliorating a symptom associated with a disease comprising administering a therapeutically effective amount of a recombinant HSV particle described above to a subject in need. Another aspect is drawn to the use of a recombinant HSV particle as described above in the preparation of a medicament for ameliorating a symptom associated with a disease in a subject in need. Again, any disease known or reasonably suspected to have a symptom amenable to application of a specifically targeted HSV is contemplated, including any disease characterized by hyperproliferative cells, such as cancer. Any of the heterologous peptide ligands (or binding pair members) and cell-surface binding partners described above in the context of describing the recombinant HSV particles is suitable for use in the method.

Another aspect of the invention is directed to a method of delivering a therapeutically useful peptide to a cell comprising: (a) inserting a therapeutically useful polynucleotide, such as an expression control element, an rDNA, or a coding region for a therapeutically useful peptide, into the DNA of a recombinant HSV particle as described above, thereby producing a recombinant HSV clone; and (b) delivering a therapeutically effective amount of the recombinant HSV clone to the cell. In a related aspect, the invention provides for the use of a recombinant HSV clone comprising a recombinant HSV particle according to claim 1 in the preparation of a medicament for delivering a therapeutically useful peptide to a cell comprising inserting a coding region for a therapeutically useful peptide into the DNA of the recombinant HSV particle, thereby producing the recombinant HSV clone. Each of the method and use comprehends delivery of the recombinant HSV clone in vivo, ex vivo, or in vitro. Any of the heterologous peptide ligands (or binding pair members) and cell-surface binding partners described above in the context of describing the recombinant HSV particles is suitable for use in the method or use.

Another aspect of the invention provides a method of killing a target cell, comprising contacting the target cell with a recombinant HSV particle as described above. A related aspect is the use of a recombinant HSV particle as described above in the preparation of a medicament for killing a target cell by contacting the target cell with the recombinant HSV particle. In preferred embodiments of either the method or the use, the recombinant HSV particle has an altered gD in which the V34S substitution is found. Any of the heterologous peptide ligands (or binding pair members) and cell-surface binding partners described above in the context of describing the recombinant HSV particles is suitable for use in the method or use.

In each of the above-described aspects of the invention, it is preferred that gD, or a portion thereof, maintains its membrane fusion properties, but has reduced capacity to bind HveA and/or Nectin-1.

Other features and advantages of the invention will be better understood by reference to the brief description of the drawing and the description of the illustrative embodiments that follow.

BRIEF DESCRIPTION OF THE DRAWING

FIG. 2. Amino acid sequence alignment of IL13-gC, IL13-gD junction sequence, and the HS binding domain of gB. FIG. 2A. The amino-terminal sequence of IL13-gC chimeric protein (SEQ ID NO:22). The sequences upstream and downstream of the HS binding site portion are shown. IL13 was inserted between the two restriction enzyme sites that are underlined. FIG. 2B. The domain of the gB open reading frame (i.e., ORF) from which the poly lysine [poly (K)] sequence was deleted (SEQ ID NO:23). The underlined sequences (codons 68-77) were not present in gB amplified from R5107. FIG. 2C. The amino-terminal sequence of IL13-gD (SEQ ID NO:24). The first underlined sequence identifies the gD signal peptide. IL13 (bracketed by arrows) was inserted between residues 24 and 25 (underlined) of gD, between the XhoI and KpnI restriction enzyme sites.

DETAILED DESCRIPTION

Figure 1A:
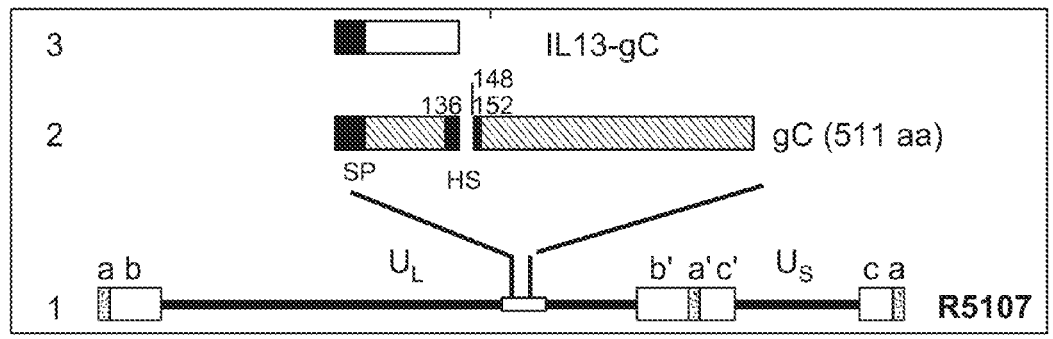
FIG. 1. Schematic representation of the HSV-1 (F) genome and gene manipulations in glycoprotein C (gC) (FIG. 1A), glycoprotein B (gB) (FIG. 1B), and glycoprotein D (gD) (FIG. 1C). Line 1, sequence arrangement of the HSV-1 genome. The rectangular boxes represent the inverted repeat sequences ab and b'a' flanking the unique long ($U_L$) sequence, and inverted repeat c'a' and ca flanking the unique short ($U_S$) sequence. Line 2, sequence arrangement of domains of the glycoprotein C; the signal peptide (SP) domain and heparan sulfate (HS)-binding domain of gC are highlighted. Line 3, human IL13 with signal peptide that replaced the N-terminal segment of 148 amino acids of gC. Line 4, sequence arrangement of the poly-lysine domain of gB. Line 5, schematic representation of a recombinant HSV-1(F) genome, in which the N-terminal domain of gC was replaced with IL13 and the polylysine domain (from codon 68 to codon 77) of gB was deleted. Line 6, sequence arrangement of glycoprotein J (gJ), glycoprotein D (gD), and glycoprotein I (gI) in $U_S$. Line 7, replacement of gD with the immediate early promoter of CMV in order to enable the expression of gI. Line 8, schematic representation of recombinant HSV-1(F) genome, in which the N-terminal domain of gC was replaced with IL13, the poly-lysine domain of gB was deleted, and IL13 was inserted after amino acid 24 of gD (FIG. 1D). Line 9, a polylinker XhoI-BglII-EcoRI-KpnI was inserted after amino acid 24 of gD, with IL13 inserted into the XhoI and KpnI sites of gD.
Figure 1B:
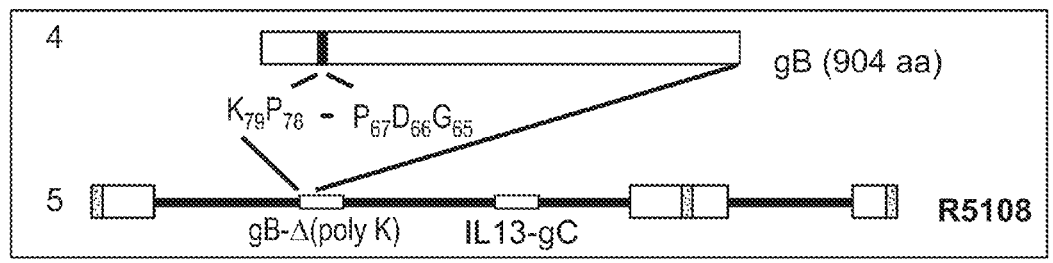
Figure 1C:
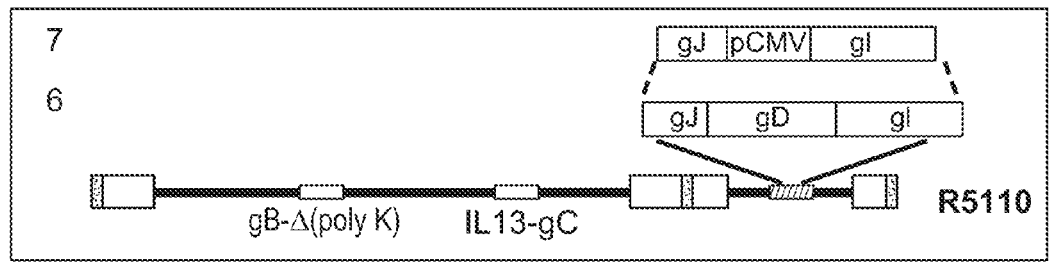
Figure 1D:
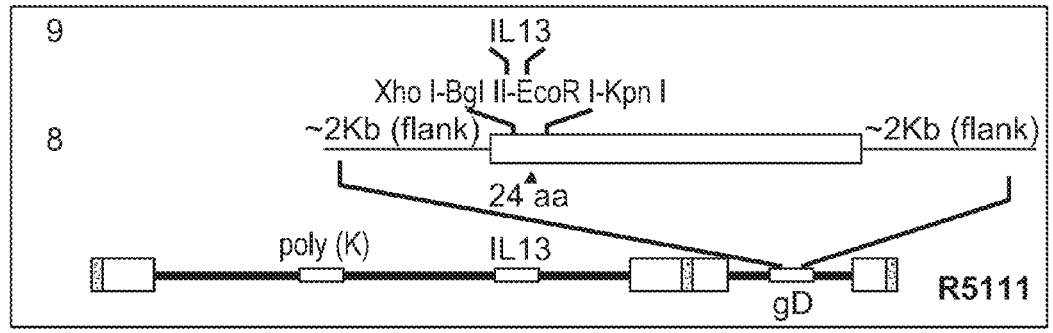

The invention provides benefits that will improve the health and well-being of animals such as man by providing a targeted approach to the treatment of a variety of conditions and diseases that currently impair health, resulting in significant economic burdens using conventional treatments. In providing modified viral particles having controllable targeting capacities, the diagnostic and therapeutic benefit of the viruses themselves can be delivered with greater precision to particular cells. Additionally, these viral particles can be used as targeting vehicles for the delivery of a wide variety of therapeutic and diagnostic biomolecules, such as polynucleotides encoding therapeutic or diagnostic peptides.

Beyond the modified viral particles, the invention provides methods for making such therapeutic and diagnostic agents as well as methods for using the agents to diagnose or treat a variety of diseases and conditions, such as tumorigenic disease (e.g., gliomas). To facilitate an understanding of the invention and all of its aspects, illustrative embodiments are described below. The descriptions of these illustrative embodiments are not meant to limit the invention to the embodiments disclosed herein. In light of the description, one of skill in the art will understand that many changes and modifications can be made to the illustrative embodiments and still remain within the invention. The illustrative embodiments are disclosed using as an exemplary virus a member of the Herpesviridae family of viruses, herpes simplex virus (HSV).

As noted above, HSV-1 and HSV-2 are members of the family of viruses known as the Herpesviridae, whose structures are well known in the art. The targeting methods of the invention are applicable to any member of the Herpesviridae and are not limited to the exemplary embodiments described in the examples. Furthermore, a large number of recombinant HSV viruses are known in the art. Such viruses may contain one or more heterologous genes. Also, such viruses may contain one or more mutated HSV genes, for example, mutations that render the virus replication-deficient or affect the virulence of the virus in one or more cell types.

Examples of recombinant HSV containing a heterologous gene and methods of making and using such viruses are described in U.S. Pat. No. 5,599,691 (incorporated herein by reference in its entirety). Preferred heterologous genes include genes encoding marker proteins. Marker proteins, such as green fluorescent protein, luciferase, and beta-galactosidase, allow detection of cells expressing the protein. In other embodiments, the heterologous gene encodes an enzyme that activates a prodrug thereby killing adjacent uninfected cells. In yet other embodiments, the heterologous gene encodes a protein that affects the immune response, such as interleukin 12 (IL-12). Such proteins that activate the immune response against a tumor are particularly useful.

In one aspect, the invention relates to altering the surface of an HSV particle to target the virus to a specific receptor. By creating a fusion protein comprising a portion of gD and a ligand (or binding pair member), the virus is targeted to a cell having a cell surface receptor that binds the ligand (or binding pair member). In preferred embodiments, one or more HSV surface proteins, such as gB (SEQ ID NOs:27 and 28), gC (SEQ ID NOs:29 and 30), or gD (SEQ ID NOs:25 and 26), are altered to reduce binding to natural HSV receptors.

"Alterations" of the surface of an HSV particle or HSV surface protein include insertions, deletions, and/or substitutions of one or more amino acid residues. One type of alteration is an insertion, which involves the incorporation of one or more amino acids into a known peptide, polypeptide or protein structure. For ease of exposition, alterations will be further described using a protein exemplar. Insertions may be located at either or both termini of the protein, or May be positioned within internal regions of known proteins, which yield proteins such as fusion proteins and proteins having amino acid tags or labels.

Another type of alteration is a deletion, wherein one or more amino acid residues in a protein are removed. Deletions can be effected at one or both termini of the protein, or with removal of one or more residues within the amino acid sequence. Deletion alterations, therefore, include all fragments of a protein described herein.

Yet another type of alteration is a substitution, which includes proteins wherein one or more amino acid residues are removed and replaced with alternative residues. In one aspect, the substitutions are conservative in nature; however, the invention embraces substitutions that are also non-conservative. Conservative substitutions for this purpose may be defined as set out in Tables A or B, below.

Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A as described in Lehninger, [Biochemistry, 2nd Edition; Worth Publishers, Inc. New York (1975), pp. 71-77] and set out immediately below.

TABLE A

Conservative Substitutions I

| SIDE CHAIN CHARACTERISTIC | AMINO ACID |
|---|---|
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternative, exemplary conservative substitutions are set out in Table B, immediately below.

TABLE B

Conservative Substitutions II

| ORIGINAL RESIDUE | EXEMPLARY SUBSTITUTION |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | thy |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The binding site of HveA has been reported to be at the amino terminal domain of gD (Carfi A., et al., 2001) The precise binding sites of gD for Nectin 1 are not known, although it has previously been reported to involve gD amino acids 38 and 221 (Manoj S., et al., 2004; Zago A., et al., 2004; Connolly S A., 2005). Accordingly, in one aspect the invention relates to amino acid alterations in the N-terminal region of gD such that the ability of gD to bind HveA or Nectin1 is reduced or eliminated A "natural receptor" as used herein is a cell surface molecule that interacts with wild-type HSV in the absence of human intervention. For example, gB and gC of HSV-1 interact with heparan sulfate proteoglycans in a natural infection. In preferred embodiments, gB and/or gC are altered to reduce or eliminate binding to heparan sulfate proteoglycans. As another example, gD is known to bind to several receptors, including HveA and Nectin-1, in a natural infection. In preferred embodiments, gD is altered to reduce or eliminate binding to HveA and/or Nectin-1.

Receptor-Ligands

As used herein, "receptor" and "ligand" refer to two members of a specific binding pair and, hence, are binding partners. A receptor is that member of the pair that is found localized on the surface of the cell; the ligand is the member of the pair that is found on the surface of HSV. Thus, in certain embodiments, the "ligand" may actually be what the art recognizes as a receptor outside the context of the invention and the "receptor" may be its respective ligand. More generally, the invention comprehends an HSV exhibiting a member of a binding pair, or a fragment thereof that retains the capacity to specifically bind the other member of the binding pair, on its surface and the other member of that binding pair, or a fragment thereof that retains the capacity to specifically bind its partner, is present on the surface of a target cell.

One advantage of the invention is the ability to tailor HSV to target a specific receptor while maintaining infectivity of the virus. In an exemplary embodiment, an HSV particle contains a fusion protein comprising a portion of gD and the cytokine IL-13. Such a virus is able to infect cells expressing the receptor IL-13Rα2. Because IL-13Rα2 is expressed on the surface of cells of malignant gliomas, HSV containing the gD/IL-13 fusion protein are effectively targeted to such cells. Ligands that bind to receptors which are overexpressed or differentially expressed on either tumor cells or cells associated with tumor growth (e.g., neovasculature) are particularly preferred. Examples include the $\alpha_v\beta_3$-$\alpha_v\beta_5$ integrins, which are overexpressed in tumor neovasculature; epidermal growth factor receptor (EGFR), which is overexpressed in head, neck, lung, colon, breast, and brain cancer cells; HER-2/Neu, which is overexpressed in breast cancer cells; MUC-1, which is overexpressed in breast, lung, and pancreas cancer cells; and prostate-specific membrane antigen, which is overexpressed in prostate cancer cells. In certain embodiments, the ligand is a single-chain antibody that binds to its cognate specific binding pair member, herein referred to as a receptor. Single-chain antibodies have been shown to be effective in targeting applications, as evidenced by their ability to target retroviruses to specific receptors.

Essentially any two binding pair members or partners may be used as receptor-ligands in the invention. However, it is contemplated that certain factors, such as the distance from the binding site on the receptor to the membrane, or the conformation of the ligand when fused to gD, may affect the efficiency of recombinant HSV fusion to the cell membrane. Therefore, screens for effective receptor-ligand pairs are contemplated, using no more than routine procedures known in the art. Additional screens, conventional in nature, may be used to optimize constructs. One routine method of screening is to follow the protocol provided in the example for candidate receptor/ligand pairs, using IL-13R/IL-13 as a control receptor/ligand pair.

Alternatively, one may use a membrane fusion assay as described in Turner et al., 1998, incorporated herein by reference in its entirety. In the Turner assay, cells transfected with construct(s) encoding gB, gH, gL, and the gD/ligand fusion protein, and cells expressing the receptor, are co-cultured and the cells are examined for membrane fusion. Membrane fusion between gD/ligand-expressing cells and receptor-expressing cells indicates that the candidate receptor-ligand pair (the ligand being a gD/ligand fusion protein) is functional. Constructs encoding functional gD/ligand proteins can then be used to create recombinant HSV that are targeted to cells expressing the receptor.

Cell Targeting

Evident from the preceding discussion, another aspect of the invention is the targeting of a recombinant HSV to a cell having a specific receptor on its surface. In preferred embodiments, a recombinant HSV is designed to comprise a ligand that interacts with a receptor known to be expressed on a cell of interest. The cell of interest is then infected with recombinant HSV. Such targeting methods may be used for a variety of purposes.

In one aspect, a recombinant HSV is used to introduce a heterologous gene into a cell that expresses the receptor. In preferred embodiments, the cell is not infected by, or is poorly infected by, wild-type HSV. Thus, in certain embodiments, the invention provides a vector for transforming a cell of interest with a heterologous gene.

Further, a cell can be rendered a target of a recombinant HSV of the invention. The cell can be rendered a target by transforming the cell to express one member of a binding pair, e.g., a receptor capable of specifically binding a ligand expressed on a recombinant HSV. For example, as described in Example 2, the J1.1 cell line, which was resistant to infection by a recombinant HSV expressing an IL-13 ligand, was rendered susceptible to infection by transforming the cell line with a vector encoding IL12Rα2 to produce the cell line J13R.

Generally, the targeted HSV according to the invention exhibit one member of a binding pair, with the other member of that pair found on the surface of a target cell. In some embodiments of the invention, targeting is achieved with a ligand-receptor binding pair, with the ligand exhibited on the targeted HSV and the cognate receptor found on the surface of the target cell, as described above. Although the invention comprehends embodiments involving binding pairs that do not exhibit a ligand-receptor relationship (e.g., biotin-avidin) and embodiments in which the receptor is exhibited by the targeted HSV (the "receptor" defined above as a "ligand" using an alternative definition of "ligand") while the cognate ligand is found on the target cell (the "ligand" defined above as a "receptor" using an alternative definition of "receptor"), embodiments in which the targeted HSV exhibits a ligand and the target cell presents the cognate receptor on its surface is used as an illustrative embodiment to reveal the versatility of the invention and to disclose the full scope thereof. For example, several ligands have been used for receptor-mediated polynucleotide transfer. Some ligands that have been characterized are asialoorosomucoid (ASOR) and transferrin (Wagner et al., Proc. Natl. Acad Sci. USA, 87(9):3410-3414, 1990). A synthetic neoglycoprotein, which recognizes the same receptor as ASOR, has also been used in a polynucleotide delivery vehicle (Ferkol et al., FASEB J., 7:1081-1091, 1993; Perales et al., Proc. Natl. Acad. Sci., USA 91:4086-4090, 1994) and epidermal growth factor (EGF) has further been used to deliver polynucleotides to squamous carcinoma cells (Myers, EPO 0273085). Each of these specific approaches, and other approaches known in the art to achieve some selectivity in DNA delivery, or targeting, are amenable to use in the compositions and methods of the invention and are contemplated as embodiments of the invention.

For embodiments in which a targeted HSV harboring a coding region, e.g., a therapeutic coding region or gene, is delivered to a target cell, the nucleic acid encoding the therapeutic gene product may ultimately be positioned and expressed at different sites. In certain embodiments, the nucleic acid encoding the therapeutic polynucleotide may be stably integrated into the genome of the cell. This integration may place the gene in its native location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or episomes encode functions sufficient to permit maintenance and replication independent of or in synchronization with the host cell cycle. How the expression construct is delivered to a cell and where in the cell the nucleic acid remains is dependent on the type of expression construct employed, as would be understood in the art.

It is envisioned that promoters subject to cell cycle regulation will be useful in the present invention. For example, in a bicistronic HSV vector designed to treat a disease, disorder or condition by killing a target cell, use of a strong CMV promoter to drive expression of a first gene, such as p16, that arrests a cell in the G1 phase is accompanied by expression of a second gene, such as p53, under the control of a promoter that is active in the G1 phase of the cell cycle, thus providing a dual-gene approach to ensure that the target cell undergoes apoptosis. Other promoters, such as those of various cyclins, PCNA, galectin-3, E2F1, p53, BRCA1, and, indeed, any suitable promoter or expression element known in the art, could be used.

In embodiments of the invention designed to treat diseases, disorders, or conditions associated with unwanted or excessive cell proliferation, such as cancer or restenosis, HSV is targeted to proliferating cells thereby killing the cells. Because HSV is lethal to infected cells, expression of a heterologous gene is not required. However, in embodiments wherein the lethality of HSV is attenuated, an HSV harboring a gene that is lethal to the infected cell or that prevents proliferation of the infected cell may be used to target a cell.

Alternatively, HSV targeted to specific surface markers can be used to visualize the distribution of tumor cells in tissues. This diagnostic tool had been unavailable because of the indiscriminate binding of HSV to cells. Modification of HSV by eliminating (ablating) or reducing the indiscriminate binding of HSV to heparan sulfate proteoglycans without deleteriously affecting the capacity of such HSV to replicate in both dividing and non-dividing cells makes possible the use of these modified viral forms to visualize the distribution of tumor cells.

In one preferred method for visualizing the distribution of tumor cells, radioactive visualization is achieved by viral thymidine kinase (TK)-dependent incorporation of a radioactive precursor. Methods of molecular imaging of gene expression are well known in the art. Methods often use highly sensitive detection techniques such as positron emission tomography (PET) or single-photon emission-computed tomography (SPECT). In one embodiment, TK expression is measured using a gancyclovir analog, such as 9-(3-[$^{18}$F]fluoro-1-hydroxy-2-propoxy)methylguanine, as the tracer or marker (Vries et al., 2002). For a review of imaging TK gene expression using PET or SPECT, see Sharma et al., 2002 or Vries et al., 2002.

A second preferred imaging method is to fuse a non-critical tegument protein (e.g. $U_S11$, which is present in nearly 2000 copies per virus particle) to a marker protein, such as green fluorescent protein, which is capable of being visualized in vivo. Alternatively, a non-critical protein can be fused to a luciferase and the presence of the luciferase visualized with a luminescent or chromatic luciferase substrate. Although a marker protein can be fused to essentially any viral structural protein, preferred viral proteins include gC, gE, gI, gG, gJ, gK, gN, $U_L11$, $U_L13$, $U_L14$, $U_L21$, $U_L41$, $U_L35$, $U_L45$, $U_L46$, $U_L47$, $U_L51$, $U_L55$, $U_L56$, $U_S10$, and $U_S11$. The marker protein also may be fused to thymidine kinase (Soling et al., 2002).

Library Screening

As noted above, HSV comprising a gD/ligand fusion protein can bind and infect cells expressing a receptor to the ligand. In one embodiment, a cell line expressing a receptor is used in screening for ligands of the receptor. cDNA from a cDNA library is cloned into a vector encoding a portion of gD to produce a gD/cDNA-encoded fusion protein. The resulting vectors are then screened for membrane fusion using the assay of Turner et al. described above or by creating recombinant HSV expressing the gD/cDNA-encoded fusion protein and screening the viruses for the ability to infect receptor-expressing cells. Such methods may be used, e.g., to identify a ligand to an orphan receptor.

In other embodiments, mutations in, or variants of, the receptor or ligand are screened to determine whether the mutants or variants maintain the ability to interact with the respective partner. Such methods may be useful in determining the specific residues important in receptor-ligand interaction.

Therapeutic Methods

Another aspect of the invention is the use of the targeted HSV in therapeutic methods. By altering the cell-binding and infectivity properties of the virus, many routes and methods of administration become viable. For example, non-targeted HSV will bind indiscriminately to a variety of cells. Because of this property, large virus numbers are used and intravenous administration is generally not effective. However, by targeting the virus, one may lower the viral load (i.e., quantity of virus), yet maintain or increase efficacy. Furthermore, the targeted HSV can be administered intravenously and produce therapeutic effects.

Therapeutic methods of the invention include those methods wherein an HSV is targeted to a receptor of a cell that contributes to, or is the basis of, a disease or disorder. These targeted HSV can either exploit the therapeutic properties of HSV itself (e.g., the lethality of HSV to infected cells) or the targeted HSV can serve as a vector for the targeted delivery of at least one therapeutic polynucleotide, such as an expressible polynucleotide comprising a coding region. For example, in methods wherein the targeted HSV contains one or more gene products that render the virus toxic to the cell or that prevent or inhibit cell proliferation, a preferred receptor is overexpressed or selectively expressed on harmful or undesirable cells, such as cancer cells. In other embodiments, the targeted HSV encodes a gene product that provides a desired function or activity in the targeted cell, e.g., when a cell has one or more genetic defects preventing the cell from functioning properly.

Additionally, it is contemplated that a therapeutic polynucleotide (e.g., gene or coding region) of a targeted HSV may be engineered to be under the expression control of a cell- or tissue-specific expression control element, e.g., a promoter. In such embodiments, the targeted HSV provide a further enhancement to the selective treatment of a suitable disorder, disease or condition. The targeted HSV is specific for a binding partner located on the surface of those cells for which treatment is intended, and expression of the therapeutic coding region or gene borne by the targeted HSV is limited to particular cells or tissues.

As HSV has been engineered to overcome the barriers to vector-based therapies, the choice of recombinant polynucleotide to be inserted into the vector has widened to the point where a wide variety of diseases, disorders and conditions are amenable to treatment with targeted HSV. A number of diseases are amenable to polynucleotide-based therapy using HSV (see, e.g., Kennedy, et al., *Brain*. 120, 1245-1259, 1997, incorporated by reference herein in its entirety). Though most attention has focused on cancers, there has been success in treating Parkinson's disease by expressing tyrosine hydroxylase in striatal cells, thus restoring L-dopa-induced nerve repair following axotomy of the superior cervical ganglion. Injection of a vector expressing nerve growth factor resulted in restored levels of tyrosine hydroxylase. More generally, HSV can now be used in polynucleotide-based therapy to replace missing or defective coding regions in the target cells. In the event of an inherited single-gene disorder (such as Lesch-Nyhan syndrome) where the complete DNA sequence, cause, and effect of the disorder are known, a single polynucleotide replacement mediated by targeted HSV is appropriate and contemplated. Another strategy amenable to the use of targeted HSV is the enhancement of endogenous expression levels of a gene product, e.g., a growth factor or enzyme. Yet another strategy for using targeted HSV is HSV-directed enzyme pro-drug therapy. The delivery of a drug-sensitivity gene would be beneficial in the treatment of, e.g., a malignant brain tumor, making the tumor more susceptible to conventional anti-cancer agents.

In other embodiments, the targeted HSV of the invention provide for vector-mediated delivery of anti-sense oligodeoxyribonucleotides (oligonucleotides). The oligonucleotides, short segments of DNA (e.g., 2-100 nucleotides in length), are delivered to target cells and therein bind to complementary mRNA, thus blocking the expression of specific genes within the target cells. The encoded protein fail to be synthesized, as the mRNA is not be recognized by the translational components of the cell. In preferred embodiments, a deleterious gene is targeted.

In yet other embodiments, targeted HSV are used to deliver polynucleotides, e.g., DNAs encoding gene products, that can recruit or enhance an immune system response, thereby bringing a subject's or patient's own immune system to bear in the treatment of a disease, disorder or condition known in the art to be amenable to immune system activity. For example, an increase in cellular antigen expression of tumor cells, mediated by delivery of an expressible coding region for the antigen by a targeted HSV, would enhance the immune response and increase the susceptibility of such tumor cells to host cytotoxic immunity.

In some embodiments, a targeted HSV composition of the invention is delivered to a patient at or around the site of a tumor, which is a very efficient method for counteracting clinical disease. Alternatively, systemic delivery of targeted HSV compositions may be appropriate in other circumstances, for example, where extensive metastasis has occurred, or where inaccessible tumors are encountered.

It is contemplated that in certain embodiments of the invention a protein that acts as an angiogenesis inhibitor is targeted to a tumor. Also, an angiogenesis inhibitor agent may be administered in combination with a targeted HSV of the invention. These agents include, for example, Marimastat (British Biotech, Annapolis Md.; indicated for non-small cell lung, small cell lung and breast cancers); AG3340 (Agouron, LaJolla, Calif.; for glioblastoma multiforme); COL-3 (Collagenex, Newtown Pa.; for brain tumors); Neovastat (Aeterna, Quebec, Canada; for kidney and non-small cell lung cancer) BMS-275291 (Bristol-Myers Squibb, Wallingford Conn.; for metastatic non-small cell lung cancer); Thalidomide (Celgen; for melanoma, head and neck cancer, ovarian, and metastatic prostate cancers; Kaposi's sarcoma; recurrent or metastatic colorectal cancer (with adjuvants); gynecologic sarcomas, liver cancer; multiple myeloma; CLL, recurrent or progressive brain cancer, multiple myeloma, and non-small cell lung, nonmetastatic prostate, refractory multiple myeloma, and renal cancer); Squalamine (Magainin Pharmaceuticals Plymouth Meeting, PA; non-small cell lung cancer and ovarian cancer); Endostatin (EntreMEd, Rockville, Md.; for solid tumors); SU5416 (Sugen, San Francisco, Calif.; recurrent head and neck, advanced solid tumors, stage IIIB or IV breast cancer; recurrent or progressive brain (pediatric) cancer; ovarian cancer, AML (acute myeloid leukemia); glioma, advanced malignancies, advanced colorectal cancer, von-Hippel Lindau disease, advanced soft tissue cancer; prostate cancer, colorectal cancer, metastatic melanoma, multiple myeloma, malignant mesothelioma: metastatic renal, advanced or recurrent head and neck cancer, metastatic colorectal cancer); SU6668 (Sugen San Francisco, Calif.; advanced tumors); interferon-α; Anti-VEGF antibody (National Cancer Institute, Bethesda Md.; Genentech San Franscisco, Calif., for refractory solid tumors; metastatic renal cell cancer, in untreated advanced colorectal cancer; EMD121974 (Merck KCgaA, Darmstadt, Germany, for HIV-related Kaposi's sarcoma, and progressive or recurrent Anaplastic Glioma); Interleukin 12 (Genetics Institute, Cambridge, Mass., for Kaposi's sarcoma) and IM862 (Cytran, Kirkland, Wash., for ovarian cancer, untreated metastatic cancers of colon and rectal origin, and Kaposi's sarcoma). The parenthetical information following the agents indicates the cancers against which the agents are being used in these trials. It is contemplated that any of these disorders may be treated with the targeted HSV compositions of the invention, either alone or in combination with the agents listed.

In order to prepare a therapeutic composition for clinical use, it will be necessary to prepare the therapeutic composition as a pharmaceutical composition, i.e., in a form appropriate for in vivo applications. Generally, this will entail preparing compositions that are essentially free of pyrogens, as well as other impurities that could be harmful to humans or other vertebrates.

Generally, appropriate salts and buffers are included to render delivery vectors stable and to allow for uptake by target cells. Aqueous compositions of the invention comprise an effective amount of the targeted HSV, dissolved or dispersed in a pharmaceutically acceptable carrier or aqueous medium. Such compositions also are referred to as inocula. The phrase "pharmaceutically acceptable" or "pharmacologically acceptable" refer to molecular entities and compositions that do not produce adverse, allergic, or other untoward reactions when administered to an animal or a human. As used herein, "pharmaceutically acceptable carriers" includes any and all solvents, dispersion media, coatings, antibacterial and antifungal agents, isotonic and absorption delaying agents, and the like. The use of such media and agents for pharmaceutically active substances is well known in the art. Unless a conventional medium or agent is incompatible with either the vectors of the invention or the intended subject receiving treatment, its use in therapeutic compositions is contemplated. Supplementary active or inert ingredients also can be incorporated into the compositions.

The active compositions of the invention include standard pharmaceutical preparations. Administration of these compositions according to the invention is by any known route, provided that the target tissue is accessible via that route. The pharmaceutical compositions may be introduced into the subject by any conventional method, e.g., by intravenous, intradermal, intramusclar, intramammary, intraperitoneal, intrathecal, retrobulbar, intravesicular, intrapulmonary (e.g., term release); sublingual, nasal, anal, vaginal, or transdermal delivery, or by surgical implantation at a particular site. The treatment may consist of a single dose or a plurality of doses over a period of time.

Upon formulation, solutions are administered in a manner compatible with the dosage formulation and in such amount as is therapeutically effective. Appropriate dosages may be ascertained through the use of established routine assays. As studies are conducted, further information will emerge regarding optimal dosage levels and duration of treatment for specific diseases, disorders, and conditions.

In preferred embodiments, the unit dose may be calculated in terms of the dose of viral particles being administered. Viral doses are defined as a particular number of virus particles or plaque forming units (pfu). Particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10- to 100-fold) due to the presence of infection-defective particles, which is determinable by routine assays known in the art.

The pharmaceutical compositions and treatment methods of the invention are useful in the fields of human medicine and veterinary medicine. Thus, the subject to be treated may be a vertebrate, e.g., a mammal, preferably human. For veterinary purposes, subjects include, for example, farm animals such as cows, sheep, pigs, horses and goats, companion animals such as dogs and cats, exotic and/or zoo animals, laboratory animals including mice, rats, rabbits, guinea pigs and hamsters; and poultry such as chickens, turkey, ducks and geese.

In some embodiments of the invention, it is contemplated that the targeted HSV is administered in conjunction with chemo- or radiotherapeutic intervention, immunotherapy, or with any other therapy conventionally employed in the treatment of cancer.

To kill cells, inhibit cell growth, inhibit metastasis, inhibit angiogenesis or otherwise reverse or reduce malignant phenotypes using the methods and compositions of the invention, one contacts a "target" cell, a tumor, or its vasculature with a targeted HSV composition and at least one other agent. The components of these compositions are provided in a combined amount effective to kill or inhibit proliferation of cancer cells. This process may involve contacting the cells with the targeted HSV composition and the agent(s) or factor(s) at the same time. This may be achieved by contacting the subject organism, or cell of interest, with a single composition or pharmacological formulation that includes both agents, or by contacting the cell with two distinct compositions or formulations, at the same or different times, wherein one composition includes a targeted HSV composition of the invention and the other composition includes the second agent.

Another aspect of the invention provides diagnostic methods that involve imaging a tumor or diseased tissue using a targeted HSV. Such methods are useful in diagnosing a patient with a disease, disorder, or condition that is indicated by the presence of a receptor on the surface of a cell. Diagnostic imaging methods are discussed above.

Kits

Kits according to the invention may include recombinant viruses of the invention or may include vectors for producing such recombinant viruses. A vector for producing a recombinant virus of the invention may encode the gD/ligand fusion protein or may be designed to facilitate cloning of a ligand to produce a gD/ligand fusion protein (e.g., a vector containing a multiple cloning site within the gD coding region that facilitates in-frame insertions).

Other components that can be included in a kit of the invention include a receptor-expressing cell line (useful as a control), a nucleic acid molecule for expressing the receptor in a particular cell type, and instructions for using the kit to effect diagnostic analyses or therapeutic treatments. In certain embodiments, a therapeutic kit will further contain a component for bringing about a therapeutic effect, such as a prodrug or a toxic compound. In other embodiments, a diagnostic kit will contain a compound useful in imaging methods, such as a chromophore or fluorophore, or an antibody for detecting infected cells.

Having provided a general description of the various aspects of the invention, the following disclosure provides examples illustrative of the invention, wherein Example 1 describes construction of a targeted HSV, Example 2 illustrates the construction of a cell line expressing a targeted HSV, and Example 3 describes the controlled infection of a desired cell by a targeted HSV.

Example 1

Construction of HSV Targeting Vector R5111

A targeted HSV was constructed to target the recombinant virus to cells of malignant gliomas. The target for entry of the virus into such cells is the IL13Rα2 receptor known to be present in malignant gliomas. Unlike the more prevalent IL13αR1 receptor, the IL13Rα2 receptor has a shorter cytoplasmic domain and does not interact with IL4, of which IL13 is a close relative. In general, the construction of the targeted HSV involved mutagenizing gB and gC to preclude their interaction with heparan sulfate. Also, IL13 was inserted into gD at amino acid 24 thereby disrupting the gD binding site for HveA. The resulting IL13-gD chimeric virus can use IL13Rα2 for entry into cells carrying that receptor.

More specifically, the targeted HSV R5111 was constructed in several steps depicted in the four panels of FIG. 1 and detailed below.

(i) Substitution of Amino Terminal Domain of gC with IL13 Fused to the Signal Sequence of gC.

FIG. 1A, lines 1-3 schematically depicts a cDNA consisting of the IL13 coding sequence fused at its amino terminus to its signal sequence. The complete cDNA of IL 13, with the N-terminal signal peptide coding region, was amplified using the PCR primer elongation method. The primers were as follows:

pIL13F1,

```
                                   (SEQ ID NO: 1)
CATTGCTCTCACTTGCCTTGGCGGCTTTGCCTCCCCAGGCCCTGTGC
CTCCCTCTACAGC;
``` pIL13F2,

```
                                   (SEQ ID NO: 2)
GCAGCTAGCCTCATGGCGCTTTTGTTGACCACGGTCATTGCTCTCAC
TTGCCTTGGCGGC;
``` and pIL13REcoRI,

```
                                   (SEQ ID NO: 3)
       GAGCTCGGATCCTGAATTCAACCGTCCCTC.
```

First-round PCR used pIL13F1 and pIL13REcoRI as primers, with pRB5830 (containing the IL13 coding region) as the template. The PCR reaction mixture was then diluted 10-fold and 1 μl of the diluted reaction mixture was used as template for the second round of PCR amplifications with pIL13F2 and pIL13REcoRI as the primer set. The PCR product was gel-purified, digested with NheI/EcoRI, and ligated into pBluescript II KS(+) at XbaI/EcoRI sites to generate pRB5832. To construct the transfer plasmid pRB5835, a 4.8-kbp HindIII/SacI fragment containing the HSV-1 gC coding region was released from cosmid pBC1007 and inserted into pBluescript II KS(+) to generate pRB5833. pRB5833 was cleaved with NheI and EcoRI and the N-terminal 148 residues of gC were replaced with the gC-signal/IL13 chimeric sequence (pRB5834). The insert in pRB5834 was released by XhoI/SacI digestion and ligated into pKO5Y at the same sites to generate pRB5835.

The recombinant virus R5107 (FIG. 1A, line 1) carrying the IL13-gC chimera was generated with the aid of the BAC-HSV system. RR1 competent cells that harbored bacterial artificial chromosome (BAC)-HSV bacmids were transformed with the transfer plasmid pRB5835 by electroporation. After incubation for 1 hour at 30° C. in LB broth, the transformed bacteria were plated on pre-warmed Zeocine (Zeo) plus chloramphenicol (Cm) (20 µg/ml of each) plates and incubated overnight at 43° C. for integration. The next day, six colonies were picked and each was separately diluted in 1 ml LB. Five pi of the diluted bacteria were then plated on Cm/10% sucrose (Suc) plates, and incubated at 30° C. overnight. To further confirm the loss of the replacement vector, 24 Cm/Suc-resistant colonies (four colonies from each plate) were restreaked in duplicate on Cm LB and Zeo LB plates, respectively. The $Suc^r/Cm^r/Zeo^r$ colonies were further screened by PCR (95° C., 4 minutes for cycle 1; then 35 cycles of 94° C., 1 minute; 60° C., 1 minute; and 72° C., 1 minute). The primers were:
pgC-F, (SEQ ID NO: 4)
GACACGGGCTACCCTCACTATCGAGGGC;

from nt 96158 to 96185 in HSV-1 strain 17),
and pgC-R, (SEQ ID NO: 5)
GGTGATGTTCGTCAGGACCTCCTCTAGGTC;

from nt 96859 to 96830 in HSV-1 strain 17).

The DNA fragment amplified from PCR-positive clones (FIG. 2B) was sequenced to further confirm the integration of IL13 in the correct open reading frame (ORF) of gC. To verify the viability of the recombinant (R5607), the recombinant BAC-HSV DNA was prepared as described elsewhere (Ye et al., 2000) and transfected into rabbit skin cells by Lipofectamine reagent (Life Technologies, Grand Island, N.Y.). The resultant virus, R5607, was stored at −80° C.

(ii) Deletion of the Polylysine Track from gB, FIG. 1 Panel B.

To make a transfer plasmid for the deletion of the gB heparan sulfate binding domain (polylysine), a 4.76 kbp BstEII fragment (from nt 53164 to 57923 of HSV-1) containing the $U_L27$ (gB) ORF released from cosmid BC1014 was blunt-ended and cloned into pBluescript II KS (+) at a SmaI site to generate pRB5846. To construct pRB5847, from which the 10-amino-acid polylysine domain of gB was deleted, two fragments flanking the polylysine domain were amplified by PCR from pRB5846. The primer sets were:
pgB1BamHI:

(SEQ ID NO: 6)
GTTCTTCTTCGGTTTCGGATCCCCCG;

pgB2BspEI:

(SEQ ID NO: 7)
CGGCATTTCCGGAATAACGCCCACTC;

and pgB3BamHI:

(SEQ ID NO: 8)
CAGAAAACCGGATCCCCCAAAGCCGCC;

pgB4BsiWI:

(SEQ ID NO: 9)
GCCAACACAAACTCGTCGTACGGGTAC.

PCR amplified fragments were then cut with BspEI/BamHI, or BsiWI/BamHI and ligated into pRB5846, which had the 1.2 kbp BsiWI/BspEI fragment already deleted. To generate the transfer plasmid pRB5848, the 4.76 kbp insert in pRB5847 was released by XbaI/EcoRV digestion and ligated into pKO5Y at the sites of XbaI and Scat Recombinant HSV-1 virus R5108 is based on R5107 with the additional deletion of the gB heparan sulfate binding domain. It was made by the same procedure as BAC-R5607, except that the transfer plasmid pRB5848 was used instead of BAC-HSV wild-type and pRB5835. The sequence of the mutant gB was verified by sequencing the entire ORF.

(iii) Deletion of gD (FIG. 1 Panel C, Lines 6 and 7).

Figure 6:
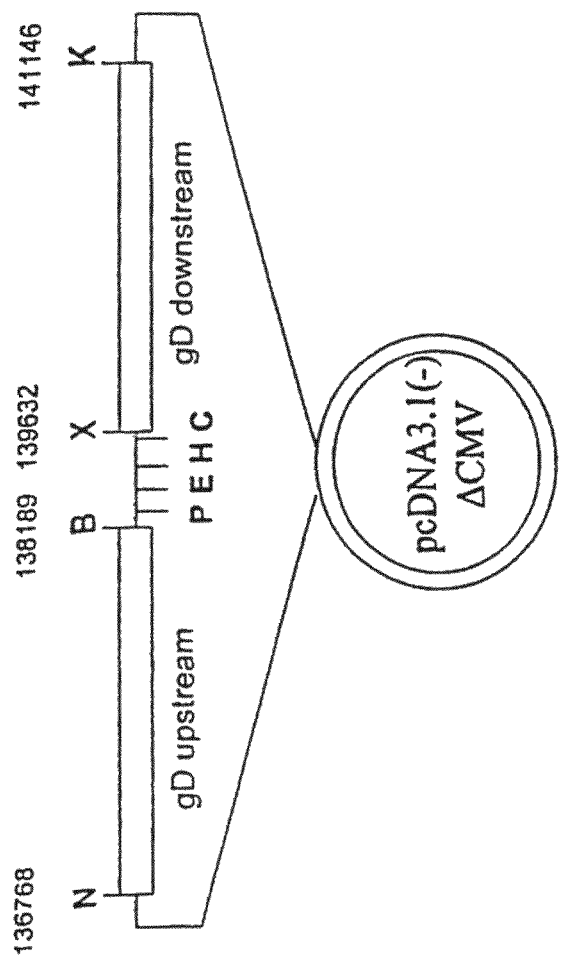
FIG. 6. Diagram of the pgD-vector.

The coding sequence of gD was replaced with the human cytomagolovirus immediate early promoter to enable the expression of glycoprotein I. A 0.65 kbp fragment containing the promoter was released from pRB5836 by ClaI digestion and inserted into pgD⁻ (FIG. 6), a plasmid obtained from G. Campadelli-Fiume. This plasmid, containing the flanking sequences of gD but lacking the gD ORF, had been cut with ClaI to generate pRB5849. pRB5849 was then cut with NotI and PmeI and ligated into pKO5Y at the NotI and ScaI sites to generate the transfer plasmid pRB5850. Recombinant HSV-1 virus R5110 is based on R5608 with the additional deletion of gD. It was made by the same procedure as BAC-R5607 except that transfer plasmid pRB5850 was used instead of BAC-HSV wild-type and pRB5835. The recombinant BAC-HSV DNA was prepared as described in (Ye et al., 2000). The mutant virus was designated R5110.

(iv) Construction of the R5111 Mutant Carrying the IL-13-gD Chimeric Gene (FIG. 1 Panel D).

Plasmid pRB123 carries a 6,584 by BamHI J fragment containing the gD coding region and flanking sequences in the BamHI site of pBR322. To construct the IL 13-gD chimeric plasmid, pRB123 was digested with AflII and HpaI to release two fragments of 7.6 kb and 3.2 kb. The 3.2 kb fragment was further digested with FspI to release 2.5 kb and 0.7 kb fragments that contain the amino-terminal 661 bp of the gD ORF. A polylinker sequence containing the restriction sites XhoI-BglII-EcoRI-KpnI was inserted into the 0.7 kb fragment downstream of the 24th codon of gD by two PCR reactions using a first forward primer, (SEQ ID NO: 10)
5'-CAGTTATCCTTAAGGTCTCTTTTGTGTGGTG-3', and a first reverse primer, (SEQ ID NO: 11)
5'-CCGGAATTCCGGAGATCTTCCCTCGAGGACCGGAAGGTCT
TTGCCGCGAAAG-3', and a second forward primer, (SEQ ID NO: 12)
5' CCGGAATTCCGGGGTACCCTGGACCAGCTGACCGACCCTC
CGG-3', and a second reverse primer, (SEQ ID NO: 13)
5'-CGGGGGGATGCGCAGCGGGAGGGCGTACTTAC-3', respectively. After digestion of the two PCR products by EcoRI, they were ligated and amplified by PCR again to obtain the desired DNA fragment containing the polylinker insertion.

IL13 was amplified by PCR with the forward primer, (SEQ ID NO: 14)
5'-CCGCTCGAGATGGCGCTTTTGTTGACCACGG-3', and the reverse primer, (SEQ ID NO: 15)
5'-GGGGTACCGTTGAACCGTCCCTCGCGAAA-3', and then inserted into the XhoI and KpnI sites of the 0.7 kb fragment described above. This new fragment with the IL13 insertion was then ligated with the 2.5 kb and 7.6 kb fragments (see above) to generate the IL13-gD chimeric transfer plasmid, pRB13-24.

R5111 was generated by co-transfection of transfer plasmid pRB13-24 and the R5110 viral DNA into U87 glioma cells. The progeny of the transfection was plated at a high dilution on Vero and HEp-2 cell cultures to yield individual, well-spaced plaques. From each of the infected cell cultures, six single plaques were picked, frozen-thawed, sonicated, and then replated on fresh cultures of Vero or HEp-2 cells (depending on the origin of the plaque) for preparation of virus stocks and to prepare viral DNA for sequencing.

Viral DNA Extraction.

Infected cells were removed from each of the 25 cm² flasks exposed to individual plaque isolates, rinsed, and resuspended in 500 µl of Lyse-O-Lot (150 mM NaCl, 10 mM Tris, 1.5 mM $MgCl_2$ in the presence of 0.1% of NP40). Nuclei were removed by low-speed centrifugation. To the supernatant fluid were added sodium dodecyl sulfate (SDS) to 0.2%, EDTA to 5 mM and β-ME to 50 mM. The solution was then extracted twice with phenol/chloroform. Viral DNA was finally precipitated by ethanol, resuspended, and the IL13 ORF and IL13-gD chimeric reading frame were amplified by PCR with two sets of primers. The first set, designed to amplify IL13, consisted of: a forward primer, (SEQ ID NO: 16)
5'-CCGCTCGAGATGGCGCTTTTGTTGACCACGG-3', and a reverse primer, (SEQ ID NO: 17)
5'-GGGGTACCGTTGAACCGTCCCTCGCGAAA-3', which will amplify the IL13 ORF. The second set, designed to amplify the IL13-gD junction, consisted of a forward junction primer, (SEQ ID NO: 18)
5'-CCGCTCGAGATGGCGCTTTTGTTGACCACGG-3', and a reverse junction primer, (SEQ ID NO: 19)
5'-AACTGCAGGTTGTTCGGGGTGGCCGGGGG-3'.

All 12 IL13-gD PCR products were sequenced to determine whether the gD sequence contained deletions or substitutions.

Verification of the Structure of R5111

The construction of the R5111 virus is depicted in FIG. 1. The design involved replacement of the HveA binding site with the IL13 ligand to enable the recombinant virus to bind the IL13α2 receptor on cell surfaces and to delete the sequences reported to bind to heparan sulfate. Verification of the structure of R5111 was done as follows:

(i) The replacement of the amino-terminal domain of gC with IL13 and the disruption of the heparan sulfate binding site was initially verified by sequencing gC from recombinant R5107 (FIG. 2 A).

(ii) The deletion of codons 68-77 of gB was verified by sequencing the gB ORF amplified by PCR from recombinant R5108 (FIG. 2 B). The nucleotide and amino acid sequences of gB with the polylysine track deleted are set out in SEQ ID NOs.:35 and 36, respectively.

Figure 3A:
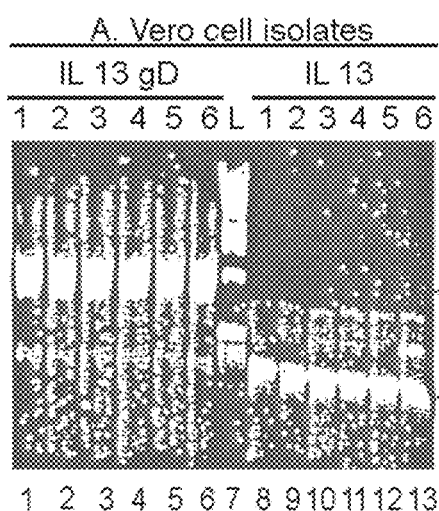
FIG. 3. Verification of R5111 viral DNA by PCR. Photographs of electrophoretically separated PCR products amplified directly from the plaques picked from Vero (FIG. 3A) and HEp-2 (FIG. 3B) cells. Viral DNAs were extracted as described in Example 1 and subjected to PCR with "IL13" primers from the IL13 ORF and IL13-gD primers, which bracketed IL13 and the gD ectodomain.
Figure 3B:
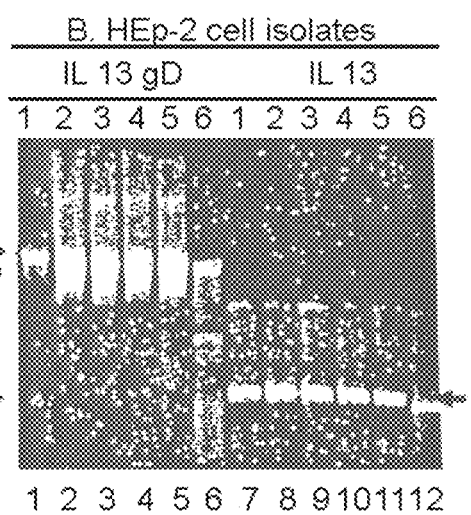

(iii) The presence of chimeric IL13-gD in R5111 was verified by PCR, as illustrated in FIG. 3, and by sequencing the entire IL13-gD coding region, amplified by PCR, as shown in FIG. 2. The nucleotide and amino acid sequences of gD with the IL13 integration are set out in SEQ ID NOs.:39 and 40, respectively. The R5111 recombinant was initially isolated from transfected U87 cells and grown in parallel in Vero cells and HEp-2 cells. To determine whether the virus grown in Vero cells or HEp-2 cells differed with respect to amino acid sequence, six plaques each from Vero or HEp-2 cultures containing well-separated plaques were picked. In this series of verification experiments, two sets of primers were used to confirm the presence of the IL13 insert in gD and to verify the presence of a junction between IL13 and gD. In a second round of verifications, the 12 clones of gD were sequenced to determine whether the isolates obtained from the viruses passaged in Vero cells or in HEp-2 cells differed in amino acid sequence. No differences were found. Furthermore, except for the inserted IL13 sequence, no differences were found between the sequence of HSV-1(F) gD and those of the cloned IL-13-gD chimeric genes (FIG. 2 C).

Figure 4A:
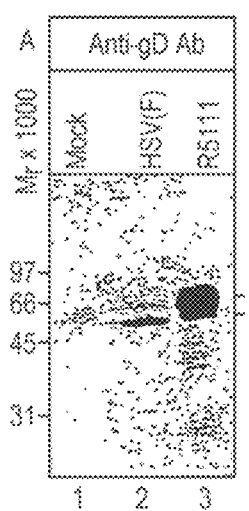
FIG. 4. Photograph of electrophoretically separated proteins from lysates of cells infected with R5111 reacted with antibody to gC, gD or IL13. HEp-2 cells grown in 25 cm$^2$ flasks were exposed to 10 PFU of HSV-1 or R5111 per cell. The cells were harvested 24 hours after infection, solubilized, subjected to electrophoresis in 10% denaturing polyacrylamide gels, electrically transferred onto a nitrocellulose sheet, and exposed to a monoclonal antibody against gD (FIG. 4A), gC (FIG. 4B) or IL13 (FIG. 4C), respectively. The protein bands corresponding to the gC, IL13-gC fusion protein, gD and the IL13-gD fusion protein are indicated. IL13-gC was the same size as native gC, as expected.
Figure 4B:
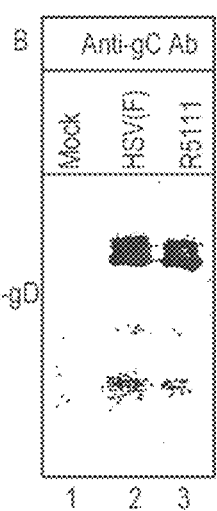
Figure 4C:
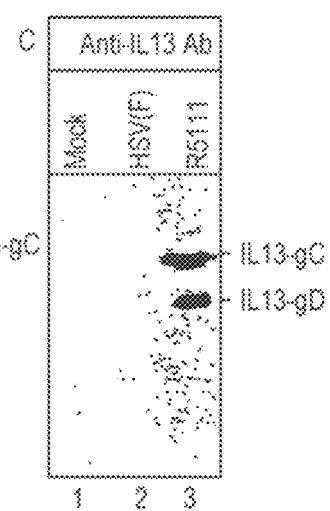
Figure 5:
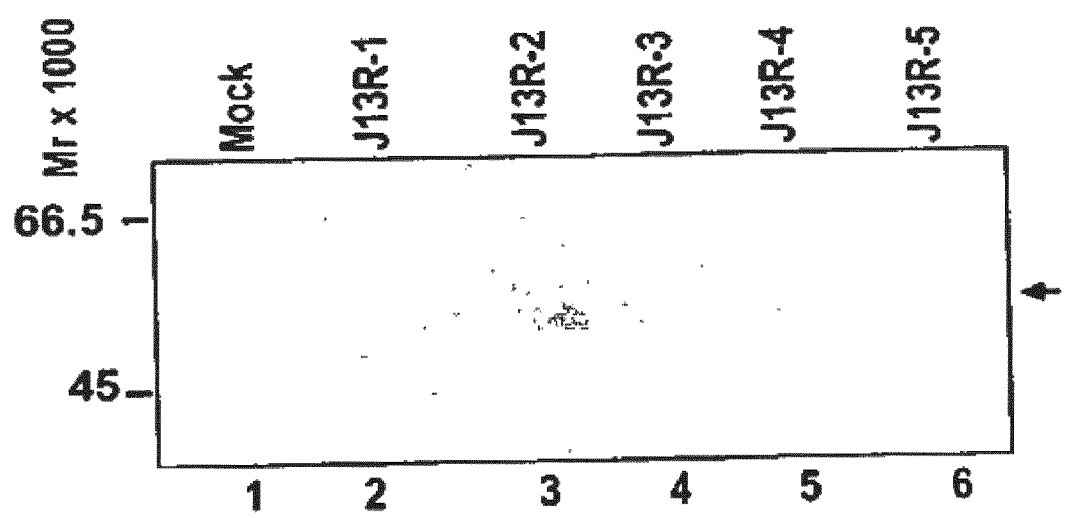
FIG. 5. HA-tagged IL13Rα2 expression from individual clones of stable transfectants of the J1.1 cell line. The individual clones were amplified as described in Example 1. Cells were harvested from 25 cm$^2$ flasks, solubilized, and subjected to electrophoresis in 12% denaturing polyacrylamide gels, electrically transferred onto a nitrocellulose sheet, and exposed to a polyclonal antibody to HA tag.

(iv) In denaturing polyacrylamide gels, IL13 migrated as a protein with an apparent Mr of 15-17,000. In the recombinant R5111, IL13 replaced 148 amino acids of gC. FIG. 4B shows an immunoblot of electrophoretically separated proteins from a lysate of R5111 mutant-infected cells exposed to an antibody to gC. As illustrated in that figure, the anti-gC antibody reacted with proteins present in lysates of HSV-1(F) and with proteins from R5111 lysates, exhibiting similar electrophoretic mobilities. In contrast, an antibody to IL13 reacted with a band of similar mobility in R5111 lysates (FIG. 4C, lane 3) but not in lysates of HSV-1(F) (FIG. 4 C, lane 2). The IL13-gD fusion protein in the R5111 mutant virus was verified by reacting the cell lysates with gD and IL13 antibody. Comparison of wild-type gD and the chimeric IL13-gD chimeric protein (FIG. 4 A, lane 3), showed that, as expected, IL13-gD migrated more slowly than the wild-type gD (FIG. 4 A, lane 2). The faster migrating band of gD did not react with the antibody to IL13 (FIG. 4C, lane 2).

Example 2

Construction of a Cell Line Expressing the IL13 Receptor (IL13Rα2)

A rigorous test of the ability of R5111 to utilize the IL13Rα2 protein as a receptor for entry required construction of a cell line expressing IL13Rα2 (nucleotides 126-1265 of SEQ ID NO.:33; SEQ ID NO:34) in the absence of other HSV-1 entry receptors. The J1.1 cell line was selected for this construction. In essence, this cell line lacks the receptors necessary for the entry of virus into cells and the cell line is not susceptible to infection by wild-type virus. The construction of a plasmid encoding a IL13Rα2 protein fused at its carboxyl terminus to a HA tag, transfection of J1.1 cells with the plasmid encoding the tagged IL13Rα2 protein, and selection of the cell line expressing the protein is described below.

To test for the production of IL13Rα2 protein, five clones of the selected cells were harvested, solubilized, subjected to electrophoresis in denaturing polyacrylamide gels and tested for expression of the protein.

Construction of J13R, a Cell Line Stably Expressing IL13Rα2 Receptor.

The IL13α2 coding region was tagged with an HA tag at its 3' end (the carboxyl terminus of the encoded polypeptide) by PCR with forward primer,

```
                                        (SEQ ID NO: 20)
5'-AAGATTTGGGC-TAGCATGGCTTTCGTTTGC-3',
``` and reverse primer,

```
                                        (SEQ ID NO: 21)
5'-TCCCTCGAAGCTTCAAGCATAATCTGGCACATCATATGTA
TCACAGAA-AAA-3'.
```

NheI and HindIII restriction digests were used to create compatible ends. The DNA fragment was then inserted into pcDNA 3.1 (zeo) vector (Invitrogen; Carlsbad, Calif.) to generate transfer plasmid pRB13-R2. All of the constructs were sequenced to insure fidelity.

J1.1, a derivative of BHK thymidine kinase$^-$ cells which lack both HveA and nectin 1 receptors, was obtained from Dr. G. Campadelli-Fiume, University of Bologna, Italy. J1.1 cells, stably transfected with pRB 13-R2 using a Lipofectamine kit (Gibco-BRL), were selected on the basis of their resistance to zeocin (Invitrogen). Zeocin-resistant clones were amplified and screened for IL13Rα2 expression by immunoblotting with anti-HA polyclonal antibody. Lysates of parental and transformed cells formed by solubilized in SDS were each electrophoretically separated in a denaturing gel (50 μg/lane), transferred to a nitrocellulose sheet, and probed with antibody against HA (Santa Cruz Biotechnology). The protein bands were visualized by an enhanced chemiluminescent detection (ECL) system (Pierce, Rockford, Ill.) according to the instructions of the manufacturer. One (J13R-2) was selected for testing the ability of R5111 to use the IL13Rα2 receptor.

As shown in FIG. 5, all clones expressed a protein band reactive with the anti-HA antibody. The apparent size of the protein was consistent with the reported size of IL13Rα2. Of 5 J13R-positive clones, J13R-2 (FIG. 5, lane 3) was selected and designated J13R.

Example 3

Infection by the HSV Targeting Vector R5111

SK-N-SH, HEp-2, Vero, and U87 cells were obtained from American Type Culture Collection (Rockville, Md.) and maintained in Dulbecco's modification of Eagle's Minimal Essential Medium (DMEM) supplemented with 10% fetal bovine serum. Replicate cultures of SK-N-SH, HEp-2, Vero, U87, J1.1, and J13R were exposed to 0.01 PFU of R5111 virus per cell. After 24 hours of incubation, the cells were harvested and viral yields were titered on Vero cells.

Immunoblotting Electrophoretically Separated Proteins.

The indicated cells were mock-infected or exposed to 10 PFU of recombinant or wild-type HSV-1(F) per cell. The cells were harvested at 24 hours after infection, disrupted in SDS disruption buffer, boiled, cleared by centrifugation and electrophoretically separated on a 10% denaturing polyacrylamide gel. After transfer to a nitrocellulose membrane, the isolated proteins were reacted with antibodies as indicated using known and conventional techniques. Monoclonal antibodies against gD- (clone H170), gC- and HA-specific polyclonal antisera were purchased from the Goodwin Institute, Plantation, Fla. Polyclonal antibodies against IL13 were purchased from Santa Cruz Biotechnology.

The results shown in Table 1 were as follows: R5111 replicated to within a 10-fold range in HEp-2, Vero, U87, and J13R cells. The titer obtained from J1.1 cells was approximately $10^5$-fold lower than that obtained from all other cell lines. To test whether the J13R cell line had acquired a receptor for wild-type HSV-1 (HSV-1(F)), J1.1 and J13R cells were also exposed to the wild-type virus. The results, also shown in Table 1, indicate that the cells remain resistant to the wild-type virus. It was known that HEp-2 cells express the nectin receptor but not the HveA receptor. The results show that the targeted HSV containing an IL13-gD fusion can target (i.e., bind and infect) cells expressing a particular receptor (IL13Rα2) approximately as well as wild-type HSV targets cells expressing the HveA receptor. The results indicate that R5111 can use IL13Rα2 as a receptor for entry in a cell line lacking all other HSV-1 receptors.

TABLE 1

Replication of R5111 in various cell lines

| Virus | Cell Line* | Yield** |
|---|---|---|
| R5111 | Vero | $11 \times 10^7$ |
| | HEp-2 | $1.2 \times 10^7$ |
| | SK-N-SH | $17 \times 10^7$ |
| | U87 | $27 \times 10^7$ |
| | J1.1 | $2 \times 10^2$ |
| | J13R | $11 \times 10^7$ |

TABLE 1-continued Replication of R5111 in various cell lines

| Virus | Cell Line* | Yield** |
|---|---|---|
| HSV-1(F) | J1.1 | $6 \times 10^3$ |
|  | J13R | $4 \times 10^3$ |

*cell lines derived from human brain tumors.
**The cells were exposed to 0.01 PFU of R5111 or HSV-1(F) per cell and harvested 24 hours after infection. Progeny virus were titered on Vero cells.

This disclosure contains an exemplary description of the construction and properties of a recombinant HSV virus, R5111. In R5111, the heparan sulfate binding sites on the surface of the viral particle were ablated to preclude or at least reduce the attachment of virus to non-targeted cells. Attachment even in the absence of fusogenic activity may lead to endocytosis, degradation of the virus particle, and to potential damage to the cell by lysosomal enzymes (Zhou et al. 2002; Zhou et al. 2000). At the same time, a copy of IL13 was inserted into gC to enhance binding of virus particles to the IL13Rα2 receptor. The major restructuring of the viral genome, consisted of insertion of IL13 at amino acid 24 of gD. Available data indicate that this modification ablates the gD binding site for the HveA receptor (Carfi et al. 2001). The data obtained using R5111 indicate that the virus retains the capacity to interact with the Nectin receptor. Nonetheless, the R5111-targeted HSV was able to infect and replicate in J13R cells but not in the parental, J1.1, cells.

Example 4

Construction of HSV Targeting Vector R5141 and R5144

A therapeutic herpes simplex virus 1 (HSV-1) capable of infecting and replicating solely in cells harboring the IL13Rα2 receptor was constructed using recombinant DNA techniques. As disclosed above, construction of R5111, which expresses IL13 on its surface and lacks the binding sites for heparin sulfate, allowed R5111 to infect 3-13R cells as well as cells exhibiting the natural receptors for HSV-1. Thus, the involvement of fusogenic glycoproteins of R5111—a key step in viral entry—is independent of the receptor with which gD interacts.

The binding site of HveA has been reported to be at the amino terminal domain of gD (Carfi A., et al., 2001). The precise binding sites of gD for Nectin 1 are not known, although it has previously been reported to involve gD amino acids 38 and 221 (Manoj S., et al., 2004; Zago A., et al., 2004; Connolly S A., 2005). The general assumption within the field is that the HveA and Nectin 1 sites do not overlap and that each independently promotes the same structural alteration of gD to enable entry of the virus into cells. However, it is possible that the surface structure of HveA and Nectin 1 at their binding sites may be similar even though the Hve1 and Nectin1 amino acid sequences are not identical.

Figure 7:
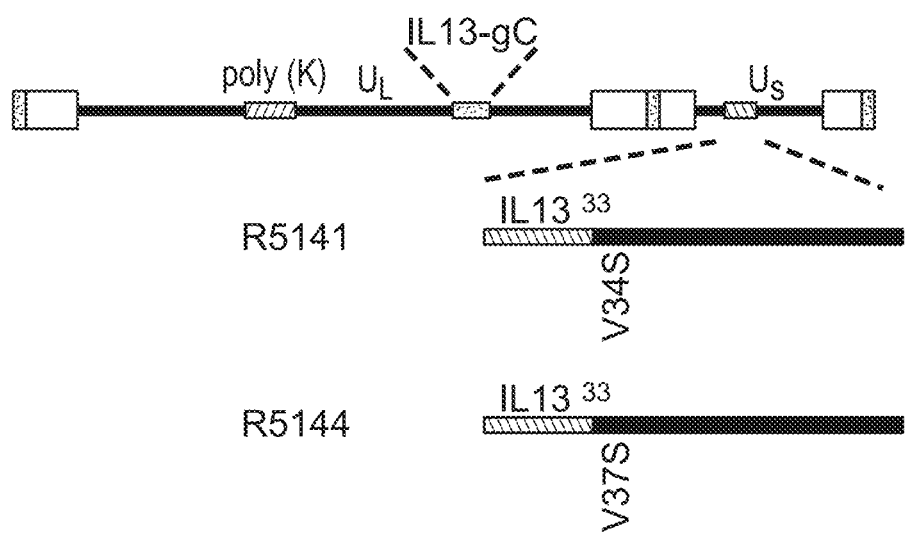
FIG. 7. Schematic representation of the HSV-1 (F) genome and genetic structure of R5141 and R5144.

Based in part on the foregoing information, viruses capable of productive replication solely in targeted cells were designed as shown in FIG. 7. Using standard molecular biological cloning techniques known in the art, recombinant virus R5141 was constructed by inserting IL13 in the place of gD residues 1-32. In addition, the valine residue at position 34 was substituted with serine ("V34S") (SEQ ID NOs.:41 and 42, respectively). Similarly, recombinant virus R5144 was constructed by inserting IL13 in the place of gD residues 1-32, and the valine at position 37 was substituted with serine ("V37S") (SEQ ID NOs.:43 and 44, respectively).

One of skill would appreciate that a variety of re-targeted SHV, both HSV-1 and HSV-2, could be constructed and assessed using routine techniques in view of the disclosures herein. In particular, substituting a binding domain of a binding partner for the N-terminal region of gD, e.g., for amino acids 1-32 of gD, would be within the skill in the art. Further alteration of the gD fusion, e.g., by amino acid substitution, whether conservative substitution or not, would also be within the skill in the art. Of course, additions or deletions to gD fusions would also be within the skill in the art and assessing the targeting capacities of such constructs would involve routine experimentation in view of the teachings herein.

Example 5

Infection by the HSV Targeting Vectors R5141 and R5144

The capacities of the recombinant viruses described in Example 4 to productively replicate solely in targeted cells were assessed using the cell lines which express either HveA (J-HveA) alone (relative to the group of HveA, Nectin1, and IL13R α2), Nectin1 (J-Nectin1) alone, or IL13Rα2 (J-13R) alone. For cell infection, the procedure set forth in Example 3 was repeated using recombinant virus R5141 and recombinant virus R5144.

The replication of R5141 and R5144 in J-Nectin-, J-HveA-, and J-13R-specific cells are summarized in Table 2. R5141 and R5144 do not productively interact with either native gD receptors, HveA or Nectin1. Significantly, however, R5141 interacts with, and replicates in IL13Rα2 for productive entry into cells.

TABLE 2

Replication of R5141 and R5144 in J-Nectin, J-HveA and J-13R cells.

|  | HSV-1 (F) | R5141 | R5144 |
|---|---|---|---|
| J-Nectin | $4 \times 10^8$ | $7 \times 10^1$ | $5 \times 10^1$ |
| J-HveA | $3 \times 10^8$ | $4 \times 10^1$ | $3 \times 10^2$ |
| J-13R | $3 \times 10^1$ | $5 \times 10^6$ | $7 \times 10^2$ |

Thus, recombinant virus R5141 is capable of productive replication solely in targeted cells and this result opens the way for development of therapeutic viruses targeting cells exhibiting the IL13Rα2 receptor, such as malignant gliomas and other human tumors exhibiting IL13Rα2. It is expected that other mutations (i.e., those that abolish binding of Nectin and those that have a similar effect on HveA) will yield viruses that enter solely via non-natural HSV receptors.

Example 6

HSV Targeting Vector R5161

An HSV targeting vector designated HSV R5161 has a structure analogous to the structure of HSV R5141, and HSV R5161 was constructed in the manner described in Example 4, above, with the exception that HSV R5161 contains the sequence encoding the HSV gD leader sequence, whereas HSV R5141 contains the sequence encoding the IL-13 leader sequence. In particular, HSV R5161 encodes an IL-13-gD fusion protein in which IL-13 sequence replaces the sequence encoding gD amino acids 1-32, with a V34S substitution in the gD moiety of the fusion protein, as described above in the context of describing HSV R5141.

The relative capacities of recombinant viruses HSV R5141 and HSV R5161 to productively replicate in targeted cells were measured in the J-13R cell line, which expresses IL13Rα2, but not HveA or Nectin1. HSV R5161 was expressed at a level 10-fold higher than the expression level of HSV R5141 in J-13R cells.

It is expected that in the majority of embodiments of the invention, relatively high levels of expression will be advantageous in ensuring that targeted cells are efficiently contacted by the re-targeted HSV. In re-targeting the HSV, the invention provides an approach to controlling the virulence of the virus in a manner that minimizes undesirable pathogenicity, i.e., pathogenicity towards non-targeted cells. In addition, the virulence of any re-targeted HSV can be further attenuated using known approaches to virulence control that do not interfere with the re-targeting, such as by mutating the $\gamma_1 34.5$ gene(s). In those embodiments in which it is desirable to have relatively high expression levels of the re-targeted HSV, it is preferred that the leader sequence of gD be used. Alternative leader sequences, such as leaders from other HSV genes, are contemplated. Moreover, expression control elements (e.g., promoters, enhancers, expression factor binding sites) can be engineered to achieve desired expression levels of the fusion protein using ordinary levels of skill and techniques known in the art.

REFERENCES

Davis F G, Freels S, Grutsch J, Barlas S, Brem S. (1998) *J. Neurosurg.* 88:1-10.
Pyles R B, Warrick R E, Chalk C L, Szanti B E, Parysek L M. (1997) *Hum Gene Ther.* 8(5):533-44.
Rampling R, Cruickshank G, Papanastassiou V, Nicoll J, Hadley D, Brennan D, Petty R, MacLean A, Harland J, McKie E, Mabbs R, Brown M. (2000) *Gene Ther.* 7(10):859-66.
McKie E A, Brown S M, MacLean A R, Graham D I. (1998) *Neuropathol. Appl Neurobiol.* 24(5):367-72.
Markert J M, Medlock M D, Rabkin S D, Gillespie G Y, Todo T, Hunter W D, Palmer C A, Feigenbaum F, Tornatore C, Tufaro F, Martuza R L. (2000) *Gene Ther.* 7(10):867-74.
Mineta T, Rabkin S D, Yazaki T, Hunter W D, Martuza R L. (1995) *Nat Med.* 1(9):938-43.
Simard C, Langlois I, Styger D, Vogt B, Vlcek C, Chalifour A, Trudel M, Schwyer M. (1995) *Virology* 212(2):734-40.
Chou J, Chen J J, Gross M, Roizman B. (1995) *Proc Natl Acad Sci USA.* 92(23):10516-20.
He B, Chou J, Brandimarti R, Mohr I, Gluzman Y, Roizman B. (1997) *J Virol.* 71(8):6049-54
Cassady K A, Gross M, Roizman B. (1998) *J Virol.* 72(9):7005-11.
Leib, D. A., Harrison, T. E., Laslo, K. M., Machalek, M. A., Moorman N. J. and Virgin, H. A W. (1999) *J. Exp. Med.* 189:663-672.
Laquerre S, Argnani R, Anderson D B, Zucchini S, Manservigi R, Glorioso J C. (1998). *J Virol.* 72(7):6119-30.
Spear, P. G., R. J. Eisenberg, and G. H. Cohen. (2000) *Virology* 275: 1-9.
Montgomery, R. I., M. S. Warner, B. J. Lum, and P. G. Spear. (1996) *Cell* 87:427-436.
Campadelli-Fiume, G., F. Cocchi, L. Menotti, and M. Lopez. (2000) *Reviews in Medical Virology.* 10:305-319.
Zhou G, Roizman B. (2002) *J Virol.* 76(12):6197-204.
Debinski W, Gibo D M, Hulet S W, Connor J R, Gillespie G Y. (1999) *Cancer Res.* 5:985-990.
Mintz A, Gibo D M, Slagle-Webb B, Christensen N D, Debinski W. (2002) *Neoplasia* 4:388-399.
Debinski W. (1998) *Crit. Rev. Oncogen.* 9:255-268.
Debinski W, Gibo D M. (2000) *Mol. Med.* 6:440-449.
Zhou G, Roizman B. (2001) *J Virol.* 75(13):6166-72.
Arsenakis M, Tomasi L F, Speziali V, Roizman B, Campadelli-Fiume G. (1986) *J Virol.* 58(2):367-76.
Ye G J, Roizman B. (2000) *Proc Natl Acad Sci USA.* 97(20):11002-7.
Zhou G, Galvan V, Campadelli-Fiume G, Roizman B. (2000) *J Virol* 74(24):11782-91.
Carfi A, Willis S H, Whitbeck J C, Krummenacher C, Cohen G H, Eisenberg R J, Wiley D C. (2001) *Mol Cell.* 8(1):169-79.
Cocchi, F., Menotti, L., Mirandola, P and Campadelli-0Fiume, G. (1998) J. Virol. 72:9992-10002.
Debinski W, Thompson J P. 1999. *Clin Cancer Res.* 5(10 Suppl):3143s-3147s.
Brooks, P. C., Clark, R. A. F., and Cheresh, D. A. Requirement of vascular integrin $\alpha_v\beta_3$ for angiogenesis. Science 264:569-571, 1994.
Brooks, P. C., Montgomery, A. M. P., Rosenfeld, M., Reisfeld, R. A., H U, T., Klier, G., and Cheresh, D. A. Integrin $\alpha_v\beta_3$ antagonists promote tumor regression by inducing apoptosis of angiogenic blood vessels. Cell 79:1157-1164, 1994.
Burger, M. J., Tebay, M. A., Keith, P. A., Samaratunga, H. M., Clements, J., Lavin, M. F., and Gardiner, R. A. Expression analysis of δ-Catenin and prostate-specific membrane antigen: Their potential as diagnostic markers for prostate cancer. Int. J. Cancer 100:228-237, 2002.
Ellerman, T. C., Domagala, T., McKem N. T. et al, Identification of the determinant of Epidermal growth factor receptor ligand-binding specificity using truncated, high affinity form of the ectodomain. 2001 Biochemistry 40 8930-8939.
Genbitsky, D. S., Bozso, Z., O'Flaharty, M. et al., 2001 A specific binding site for a fragment of the B-loop of epidermal growth factor and related peptides. Peptides 23:97-102 A.
Urbanelli, L., Ronchini, C., Fontana, L. et al., Tergeted gene transduction of mammalian cells expressing the HER2/neu receptor by filamentous phage. *J Mol Biol.* 2001 Nov. 9; 313(5):965-76.
Hayashi, T., Takahashi, T., Motoya, S., et al. MUC1 Mucin core protein binds to the dfomasin of ICAM-1 2001 Digestion 63:87-92.
Fracasso, G., Bellisola, G., Cingarlini, S., Castelletti, D., Prayer-Galletti, T., Pagano, F., Tridente, G., and Colombatti, M. Anti-tumor effects of toxins targeted to the prostate specific membrane antigen. Prostate 53:9-23, 2002.
Mabjeesh, N. J., Zhong, H., and Simons, J. W. Gene therapy of prostate cancer: current and future directions. Endo. Related Cancer 9:115-139, 2002.
Ross, S., Spencer, S. D., Holcomb, I., Tan, C., Hongo, J., Devaux, B., Rangell, L., Keller, G. A., Schow, P., Steeves, R. M., Lutz, R. J., Frantz, G., Hillan, K., Peale, F., Tobin, P., Eberhard, D., Rubin, M. A., Lasky, L. A., and Koeppen, H. Prostate stem cell antigen as therapy target: Tissue expression and in Vivo efficacy of an immunoconjugate. Cancer Res. 62:2546-2553, 2002.
Ruoslahti, E. RGD and other recognition sequences for integrins. Annu. Rev. Cell Dev. Biol. 12:697-715, 1996.
Thomas, J., Gupta, M., Grasso, Y., Reddy, C. A., Heston, W. D., Zippe, C., Dreicer, R., Kupelian, P. A., Brainard, J., Levin, H. S., and Klein, E. A. Preoperative combined nested reverse transcriptase polymerase chain reaction for prostate-specific antigen and prostate-specific membrane antigen does not correlate with pathologic stage or biochemical failure in patients with localized prostate cancer undergoing radical prostatectomy. *J. Clin. Oncol.* 20:3213-3218, 2002.

Lorimer and Lavictoire, Targeting retrovirus to cancer cells expressing a mutant EGF receptor by insertion of a single chain antibody variable domain in the envelope glycoprotein receptor binding lobe, *J Immunol Methods* 237 (1-2):147-57, 2000.

Turner et al., Glycoproteins gB, gD, and gHgL of Herpes Simplex Virus Type 1 are Necessary and Sufficient t Mediate membrane fusion in a Cos cell transfection system, *J of Virol*, 72(1): 873-75, 1998.

Brunetti et al., Herpes Simplex Virus gD and Virions Accumulate in Endosomes by Mannose 6-Phosphate-Dependent and -Independent Mechanisms, *J of Virol*, 72(4): 3330-3339, 1998.

Sharma et al., Molecular imaging of gene expression and protein function in vivo with PET and SPECT, *J Magn Reson Imaging*, 16(4):336-51, 2002.

Vries et al., Scintgraphic Imaging of HSVtk Gene Therapy, *Curr Pharm Des*, 8(16):1435-50, 2002.

Vries et al., Positron emission tomography: measurement of transgene expression, *Methods*, 27(3):234, 2002.

Soling et al., Intracellular localization of Herpes simplex virus type 1 thymidine kinase fused to different fluorescent proteins depends on choice of fluorescent tag, *FEBS Lett*, 527(1-3):153, 2002.

Zhou G., and Roizman B., *J Virol*, 9:5272-5277 (2005)

Manoj S., et al., *Proc. Natl. Acad. Sci. USA.*, 101:12414-12421 (2004);

Zago A., et al., *Proc. Natl. Acad. Sci. USA.*, 101:17498-17503 (2004);

Connolly S A., *J. Virol.*, 79:1282-1295 (2005)

---

The invention claimed is:

1. A method of targeting a recombinant HSV particle to a cell comprising
   (a) identifying a ligand for a ligand binding partner exhibited on the surface of a target cell; and
   (b) contacting the target cell with an HSV particle having at least one protein on its surface, comprising an altered gD, wherein the altered gD comprises an amino acid substitution at position 34, wherein the alteration reduces binding of gD to one or more of its cellular receptors, said alteration comprising
      (i) a heterologous peptide ligand on the surface of the recombinant HSV particle forming a fusion protein with the altered gD; and
      (ii) an amino acid alteration;
   wherein said recombinant HSV particle preferentially binds to cells expressing a binding partner to said heterologous peptide ligand, and wherein the ligand binds to the binding partner exhibited on the surface of said target cell.

2. The method of claim 1, wherein the alteration to gD reduces binding of gD to at least one cellular receptor for gD selected from the group consisting of HveA and Nectin-1.

3. The method of claim 1, wherein the ligand forms a second fusion protein with gC.

4. The method of claim 3, wherein the ligand is a cytokine.

5. The method of claim 4, wherein the cytokine is IL13.

6. The method of claim 1, wherein the amino acid alteration is a V34S amino acid substitution.

* * * * *

SEQUENCE LISTING

```
<160> NUMBER OF SEQ ID NOS: 44

<210> SEQ ID NO 1
<211> LENGTH: 60
<212> TYPE: DNA
<213> ORGANISM: Artificial sequence
<220> FEATURE:
<223> OTHER INFORMATION: Synthetic primer

<400> SEQUENCE: 1
cattgctctc acttgccttg gcggctttgc ctccccaggc cctgtgcctc cctctacagc      60

<210> SEQ ID NO 2
<211> LENGTH: 60
<212> TYPE: DNA
<213> ORGANISM: Artificial sequence
<220> FEATURE:
<223> OTHER INFORMATION: Synthetic primer

<400> SEQUENCE: 2
gcagctagcc tcatggcgct tttgttgacc acggtcattg ctctcacttg ccttggcggc      60

<210> SEQ ID NO 3
<211> LENGTH: 30
<212> TYPE: DNA
<213> ORGANISM: Artificial sequence
<220> FEATURE:
<223> OTHER INFORMATION: Synthetic primer

<400> SEQUENCE: 3
gagctcggat cctgaattca accgtccctc                                        30

<210> SEQ ID NO 4
<211> LENGTH: 28
<212> TYPE: DNA
<213> ORGANISM: Artificial sequence
<220> FEATURE:
<223> OTHER INFORMATION: Synthetic primer

<400> SEQUENCE: 4
gacacgggct accctcacta tcgagggc                                          28

<210> SEQ ID NO 5
<211> LENGTH: 30
<212> TYPE: DNA
<213> ORGANISM: Artificial sequence
```

-continued

```
<220> FEATURE:
<223> OTHER INFORMATION: Synthetic primer

<400> SEQUENCE: 5
ggtgatgttc gtcaggacct cctctaggtc                                          30

<210> SEQ ID NO 6
<211> LENGTH: 26
<212> TYPE: DNA
<213> ORGANISM: Artificial sequence
<220> FEATURE:
<223> OTHER INFORMATION: Synthetic primer

<400> SEQUENCE: 6
gttcttcttc ggtttcggat cccccg                                              26

<210> SEQ ID NO 7
<211> LENGTH: 26
<212> TYPE: DNA
<213> ORGANISM: Artificial sequence
<220> FEATURE:
<223> OTHER INFORMATION: Synthetic primer

<400> SEQUENCE: 7
cggcatttcc ggaataacgc ccactc                                              26

<210> SEQ ID NO 8
<211> LENGTH: 27
<212> TYPE: DNA
<213> ORGANISM: Artificial sequence
<220> FEATURE:
<223> OTHER INFORMATION: Synthetic primer

<400> SEQUENCE: 8
cagaaaaccg gatcccccaa agccgcc                                             27

<210> SEQ ID NO 9
<211> LENGTH: 27
<212> TYPE: DNA
<213> ORGANISM: Artificial sequence
<220> FEATURE:
<223> OTHER INFORMATION: Synthetic primer

<400> SEQUENCE: 9
gccaacacaa actcgtcgta cgggtac                                             27

<210> SEQ ID NO 10
<211> LENGTH: 31
<212> TYPE: DNA
<213> ORGANISM: Artificial sequence
<220> FEATURE:
<223> OTHER INFORMATION: Synthetic primer

<400> SEQUENCE: 10
cagttatcct taaggtctct tttgtgtggt g                                        31

<210> SEQ ID NO 11
<211> LENGTH: 52
<212> TYPE: DNA
<213> ORGANISM: Artificial sequence
<220> FEATURE:
<223> OTHER INFORMATION: Synthetic primer

<400> SEQUENCE: 11
ccggaattcc ggagatcttc cctcgaggac cggaaggtct ttgccgcgaa ag                 52
```

<210> SEQ ID NO 12
<211> LENGTH: 43
<212> TYPE: DNA
<213> ORGANISM: Artificial sequence
<220> FEATURE:
<223> OTHER INFORMATION: Synthetic primer

<400> SEQUENCE: 12
ccggaattcc ggggtaccct ggaccagctg accgaccctc cgg          43

<210> SEQ ID NO 13
<211> LENGTH: 32
<212> TYPE: DNA
<213> ORGANISM: Artificial sequence
<220> FEATURE:
<223> OTHER INFORMATION: Synthetic primer

<400> SEQUENCE: 13 cgggggatg cgcagcggga gggcgtactt ac                       32

<210> SEQ ID NO 14
<211> LENGTH: 31
<212> TYPE: DNA
<213> ORGANISM: Artificial sequence
<220> FEATURE:
<223> OTHER INFORMATION: Synthetic primer

<400> SEQUENCE: 14
ccgctcgaga tggcgctttt gttgaccacg g                       31

<210> SEQ ID NO 15
<211> LENGTH: 29
<212> TYPE: DNA
<213> ORGANISM: Artificial sequence
<220> FEATURE:
<223> OTHER INFORMATION: Synthetic primer

<400> SEQUENCE: 15
ggggtaccgt tgaaccgtcc ctcgcgaaa                          29

<210> SEQ ID NO 16
<211> LENGTH: 31
<212> TYPE: DNA
<213> ORGANISM: Artificial sequence
<220> FEATURE:
<223> OTHER INFORMATION: Synthetic primer

<400> SEQUENCE: 16
ccgctcgaga tggcgctttt gttgaccacg g                       31

<210> SEQ ID NO 17
<211> LENGTH: 29
<212> TYPE: DNA
<213> ORGANISM: Artificial sequence
<220> FEATURE:
<223> OTHER INFORMATION: Synthetic primer

<400> SEQUENCE: 17
ggggtaccgt tgaaccgtcc ctcgcgaaa                          29

<210> SEQ ID NO 18
<211> LENGTH: 31
<212> TYPE: DNA
<213> ORGANISM: Artificial sequence
<220> FEATURE:
<223> OTHER INFORMATION: Synthetic primer

```
<400> SEQUENCE: 18
ccgctcgaga tggcgctttt gttgaccacg g                                     31

<210> SEQ ID NO 19
<211> LENGTH: 29
<212> TYPE: DNA
<213> ORGANISM: Artificial sequence
<220> FEATURE:
<223> OTHER INFORMATION: Synthetic primer

<400> SEQUENCE: 19
aactgcaggt tgttcggggt ggccggggg                                        29

<210> SEQ ID NO 20
<211> LENGTH: 30
<212> TYPE: DNA
<213> ORGANISM: Artificial sequence
<220> FEATURE:
<223> OTHER INFORMATION: Synthetic primer

<400> SEQUENCE: 20
aagatttggg ctagcatggc tttcgtttgc                                       30

<210> SEQ ID NO 21
<211> LENGTH: 51
<212> TYPE: DNA
<213> ORGANISM: Artificial sequence
<220> FEATURE:
<223> OTHER INFORMATION: Synthetic primer

<400> SEQUENCE: 21
tccctcgaag cttcaagcat aatctggcac atcatatgta tcacagaaaa a               51

<210> SEQ ID NO 22
<211> LENGTH: 568
<212> TYPE: DNA
<213> ORGANISM: Herpes Simplex Virus-1

<400> SEQUENCE: 22
gcttggtcgg gaggccgcat cgaacgcaca ccccccatccg gtggtccgtg tggaggtcgt     60
ttttcagtgc ccggtctcgc tttgccggga acgctagcct catggcgctt ttgttgacca    120
cggtcattgc tctcacttgc cttggcggct ttgcctcccc aggccctgtg cctccctcta    180
cagccctcag gtacctcatt gaggagctgg tcaacatcac ccagaaccag aaggctccgc    240
tctgcaatgg cagcatggta tggagcatca acctgacagc tggcatgtac tgtgcagccc    300
tggaatccct gatcaacgtg tcaggctgca gtgccatcga aagacccag aggatgctga    360 gcggattctg cccgcacaag gtctcagctg ggcagttttc cagcttgcat gtccgagaca    420
ccaaaatcga ggtggcccag tttgtaaaag atctgctctt acatttaaag aaactttttc    480
gcgagggacg gttgaattcc acccgcatgg agttccgcct ccagatatgg cgttactcca    540
tgggtccgtc ccccccaatc gctccggc                                       568

<210> SEQ ID NO 23
<211> LENGTH: 350
<212> TYPE: DNA
<213> ORGANISM: Herpes Simplex Virus-1

<400> SEQUENCE: 23
gggtcctggt ggcgtcggcg gctccgagtt ccccccggcac gcctggggtc gcggccgcga    60
```

-continued

```
cccaggcggc gaacggggga cctgccactc cggcgccgcc cgcccctggc cccgccccaa    120
cgggggatcc gaaaccgaag aagaacagaa aaccgaaacc cccaaagcgc cgcgccccgc    180
cggcgacaac gcgaccgtcg ccgcgggcca cgccaccctg cgcgagcacc tgcgggacat    240
caaggcggag aacaccgatg caaacttttta cgtgtgccca ccccccacgg gcgccacggt    300
ggtgcagttc gagcagccgc gccgctgccc gacccggccc gagggtcaga                350

<210> SEQ ID NO 24
<211> LENGTH: 655
<212> TYPE: DNA
<213> ORGANISM: Artificial sequence
<220> FEATURE:
<223> OTHER INFORMATION: Amino-terminal sequence of IL13-gD

<400> SEQUENCE: 24
atgggggggg ctgccgccag gttgggggcc gtgattttgt ttgtcgtcat agtcggcctc     60
catggggtcc gcggcaaata tgccttggcg gatgcctctc tcaagctggc cgaccccaat    120
cgctttcgcc gcaaagacct tccggtcctc gagatggcgc ttttgttgac cacggtcatt    180
gctctcactt gccttggcgg ctttgcctcc ccaggccctg tgcctcccct ctacagccct    240
cagggagctc attgaggagc tggtcaacat cacccagaac cagaaggctc cgctctgcaa    300
tggcagcatg gtttggagca tcaacctgac agctggcatg tactgtgcag ccctggaatc    360
cctgatcaac gtgtcaggct gcagtgccat cgagaagacc cagaggatgc tgggcggatt    420
ctgcccgcac aaggtctcag ctgggcagtt ttccagcttg catgtccgag acaccaaaat    480
cgaggtggcc cagtttgtaa aggacctgct cttacattta aagaaacttt ttcgcgaggg    540
acggttcaac tgaaacggta ccctggacca gctgaccgac cctccggggg tccggcgcgt    600
gtaccacatc caggcgggcc taccggaccc gttccagccc cccagcctcc cgatc          655

<210> SEQ ID NO 25
<211> LENGTH: 1185
<212> TYPE: DNA
<213> ORGANISM: Herpes Simplex Virus-1

<400> SEQUENCE: 25
atgggggggg ctgccgccag gttgggggcc gtgattttgt ttgtcgtcat agtgggcctc     60
catggggtcc gcggcaaata tgccttggcg gatgcctctc tcaagatggc cgaccccaat    120
cgctttcgcg gcaaagacct tccggtcccg gaccggctga ccgaccctcc gggggtccgg    180
cgcgtgtacc acatccaggc gggcctaccg gacccgttcc agccccccag cctcccgatc    240
acggtttact acgccgtgtt ggagcgcgcc tgccgcagcg tgctcctaaa cgcaccgtcg    300
gaggcccccc agattgtccg cggggcctcc gaagacgtcc ggaaacaacc ctacaacctg    360
accatcgctt ggtttcggat gggaggcaac tgtgctatcc ccatcacggt catggagtac    420
accgaatgct cctacaacaa gtctctgggg gcctgtccca tccgaacgca gccccgctgg    480
aactactatg acagcttcag cgccgtcagc gaggataacc tggggttcct gatgcacgcc    540
cccgcgtttg agaccgccgg cacgtacctg cggctcgtga agataaacga ctggacggag    600
attacacagt ttatcctgga gcaccgagcc aagggctcct gtaagtacgc ccttccgctg    660
cgcatccccc cgtcagcctg cctctccccc caggcctacc agcagggggt gacggtggac    720
agcatcggga tgctgccccg cttcatcccc gagaaccagc gcaccgtcgc cgtatacagc    780
ttgaagatcg ccgggtggca cgggcccaag gccccataca cgagcaccct gctgcccccg    840
gagctgtccg agacccccaa cgccacgcag ccagaactcg ccccggaaga ccccgaggat    900
```

```
tcggccctct tggaggaccc cgtggggacg gtggtgccgc aaatcccacc aaactggcac    960
ataccgtcga tccaggacgc cgcgacgcct taccatcccc cggccacccc gaacaacatg   1020
ggcctgatcg ccggcgcggt gggcggcagt ctcctggtag ccctggtcat ttgcggaatt   1080
gtgtactgga tgcgccgccg cactcaaaaa gccccaaagc gcatacgcct ccccacatc    1140 cgggaagacg accagccgtc ctcgcaccag cccttgtttt actag                    1185
```

<210> SEQ ID NO 26
<211> LENGTH: 394
<212> TYPE: PRT
<213> ORGANISM: Herpes Simplex Virus-1

<400> SEQUENCE: 26

```
Met Gly Gly Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Pro Asp Arg Leu Thr Asp Pro Pro Gly Val Arg Arg Val Tyr His
    50                  55                  60

Ile Gln Ala Gly Leu Pro Asp Pro Phe Gln Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Val Tyr Ser Leu Lys Ile Ala Gly Trp His Gly Pro Lys Ala Pro
            260                 265                 270

Tyr Thr Ser Thr Leu Leu Pro Pro Glu Leu Ser Glu Thr Pro Asn Ala
        275                 280                 285

Thr Gln Pro Glu Leu Ala Pro Glu Asp Pro Glu Asp Ser Ala Leu Leu
    290                 295                 300

Glu Asp Pro Val Gly Thr Val Val Pro Gln Ile Pro Pro Asn Trp His
305                 310                 315                 320
```

```
Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Val Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390

<210> SEQ ID NO 27
<211> LENGTH: 2715
<212> TYPE: DNA
<213> ORGANISM: Herpes Simplex Virus-1

<400> SEQUENCE: 27
atgcgccagg gcgccccccgc gcggggggcgc cggtggttcg tcgtatgggc gctcttgggg    60
ttgacgctgg gggtcctggt ggcgtcggcg gctccgagtt cccccggcac gcctggggtc    120
gcggccgcga cccaggcggc gaacgggggc cctgccactc cggcgccgcc cgcccctggc    180 gccccccaa cggggggaccc gaaaccgaag aagaacagaa accgaaaccc ccaaagccg      240 ccgcgccccg ccggcgacaa cgcgaccgtc gccgcgggcc acgccaccct gcgcgagcac    300
ctgcgggaca tcaaggcgga gaacaccgat gcaaactttt acgtgtgccc acccccacg    360 ggcgccacgg tggtgcagtt cgagcagccg cgccgctgcc cgacccggcc cgagggtcag    420
aactacacgg agggcatcgc ggtggtcttc aaggagaaca tcgccccgta caagttcaag    480
gccaccatgt actacaaaga cgtcaccgtt cgcaggtgt ggttcggcca ccgctactcc    540
cagtttatgg ggatctttga ggaccgcgcc cccgtcccct cgaggaggt gatcgacaag    600 atcaacgcca aggggggtctg tcggtccacg gccaagtacg tgcgcaacaa cctggagacc    660
accgcgtttc accgggacga ccacgagacc gacatggagc tgaaaccggc caacgccgcg    720
acccgcacga gccgggggctg gcacaccacc gacctcaagt acaacccctc gcgggtggag    780
gcgttccacc ggtacgggac gacggtaaac tgcatcgtcg aggaggtgga cgcgcgctcg    840
gtgtacccgt acgacgagtt tgtgttggcg actggcgact tgtgtacat gtccccgttt    900 tacggctacc gggaggggtc gcacaccgaa cacaccagct acgccgccga ccgcttcaag    960
caggtcgacg gcttctacgc gcgcgacctc accaccaagg cccgggccac ggcgccgacc    1020
acccggaacc tgctcacgac ccccaagttc accgtggcct gggactgggt gccaaagcgc    1080
ccgtcggtct gcaccatgac caagtggcag gaggtggacg agatgctgcg ctccgagtac    1140
ggcggctcct tccgattctc ttccgacgcc atatccacca ccttcaccac caacctgacc    1200
gagtacccgc tctcgcgcgt ggacctgggg gactgcatcg gcaaggacgc ccgcgacgcc    1260
atggaccgca tcttcgcccg caggtacaac gcgacgcaca tcaaggtggg ccagccgcag    1320
tactacctgg ccaatggggg ctttctgatc gcgtaccagc cccttctcag caacacgctc    1380
gcggagctgt acgtgcggga acacctccgc gagcagagcc gcaagccccc aaaccccacg    1440 ccccccgccgc ccggggccag cgccaacgcg tccgtggagc gcatcaagac cacctcctcc    1500
atcgagttcg ccaggctgca gtttacgtac aaccacatac agcgccatgt caacgatatg    1560
ttgggccgcg ttgccatcgc gtggtgcgag ctgcagaatc acgagctgac cctgtggaac    1620
gaggcccgca agctgaaccc caacgccatc gcctcggcca ccgtgggccg gcgggtgagc    1680
```

-continued

```
gcgcggatgc tcggcgacgt gatggccgtc tccacgtgcg tgccggtcgc cgcggacaac    1740
gtgatcgtcc aaaactcgat gcgcatcagc tcgcggcccg gggcctgcta cagccgcccc    1800
ctggtcagct ttcggtacga agaccagggc ccgttggtcg aggggcagct gggggagaac    1860
aacgagctgc ggctgacgcg cgatgcgatc gagccgtgca ccgtgggaca ccggcgctac    1920
ttcaccttcg gtgggggcta cgtgtacttc gaggagtacg cgtactccca ccagctgagc    1980
cgcgccgaca tcaccaccgt cagcaccttc atcgacctca acatcaccat gctggaggat    2040
cacgagtttg tcccctgga ggtgtacacc cgccacgaga tcaaggacag cggcctgctg    2100
gactacacgg aggtccagcg ccgcaaccag ctgcacgacc tgcgcttcgc cgacatcgac    2160
acggtcatcc acgccgacgc caacgccgcc atgtttgcgg gcctgggcgc gttcttcgag    2220
gggatgggcg acctggggcg cgcggtcggc aaggtggtga tgggcatcgt gggcggcgtg    2280
gtatcggccg tgtcgggcgt gtcctccttc atgtccaacc cctttggggc gctggccgtg    2340
ggtctgttgg tcctggccgg cctggcggcg gccttcttcg cctttcgcta cgtcatgcgg    2400
ctgcagagca acccccatgaa ggccctgtac ccgctaacca ccaaggagct caagaacccc    2460
accaacccgg acgcgtccgg ggagggcgag gagggcggcg actttgacga ggccaagcta    2520
gccgaggccc gggagatgat acggtacatg gccctggtgt ctgccatgga gcgcacggaa    2580
cacaaggcca agaagaaggg cacgagcgcg ctgctcagcg ccaaggtcac cgacatggtc    2640
atgcgcaagc gccgcaacac caactacacc caagttccca caaagacgg tgacgccgac    2700
gaggacgacc tgtga                                                    2715
```

<210> SEQ ID NO 28
<211> LENGTH: 904
<212> TYPE: PRT
<213> ORGANISM: Herpes Simplex Virus-1

<400> SEQUENCE: 28

```
Met Arg Gln Gly Ala Pro Ala Arg Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Thr Gln Ala Ala Asn
        35                  40                  45

Gly Gly Pro Ala Thr Pro Ala Pro Pro Ala Pro Gly Ala Pro Pro Thr
    50                  55                  60

Gly Asp Pro Lys Pro Lys Lys Asn Arg Lys Pro Lys Pro Pro Lys Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190
```

```
Pro Phe Glu Glu Val Ile Asp Lys Ile Asn Ala Lys Gly Val Cys Arg
            195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
        290                 295                 300

Glu Gly Ser His Thr Glu His Thr Ser Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
        370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Leu Ala Asn Gly Gly Phe
        435                 440                 445

Leu Ile Ala Tyr Gln Pro Leu Leu Ser Asn Thr Leu Ala Glu Leu Tyr
        450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
    530                 535                 540

Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605
```

| Gln | Gly | Pro | Leu | Val | Glu | Gly | Gln | Leu | Gly | Glu | Asn | Asn | Glu | Leu | Arg |
|---|---|---|---|---|---|---|---|---|---|---|---|---|---|---|---|
| | 610 | | | | 615 | | | | | 620 | | | | | |

| Leu | Thr | Arg | Asp | Ala | Ile | Glu | Pro | Cys | Thr | Val | Gly | His | Arg | Arg | Tyr |
|---|---|---|---|---|---|---|---|---|---|---|---|---|---|---|---|
| 625 | | | | | 630 | | | | | 635 | | | | | 640 |

| Phe | Thr | Phe | Gly | Gly | Gly | Tyr | Val | Tyr | Phe | Glu | Glu | Tyr | Ala | Tyr | Ser |
|---|---|---|---|---|---|---|---|---|---|---|---|---|---|---|---|
| | | | | 645 | | | | | 650 | | | | | 655 | |

| His | Gln | Leu | Ser | Arg | Ala | Asp | Ile | Thr | Thr | Val | Ser | Thr | Phe | Ile | Asp |
|---|---|---|---|---|---|---|---|---|---|---|---|---|---|---|---|
| | | | 660 | | | | | 665 | | | | | 670 | | |

| Leu | Asn | Ile | Thr | Met | Leu | Glu | Asp | His | Glu | Phe | Val | Pro | Leu | Glu | Val |
|---|---|---|---|---|---|---|---|---|---|---|---|---|---|---|---|
| | | 675 | | | | | 680 | | | | | 685 | | | |

| Tyr | Thr | Arg | His | Glu | Ile | Lys | Asp | Ser | Gly | Leu | Leu | Asp | Tyr | Thr | Glu |
|---|---|---|---|---|---|---|---|---|---|---|---|---|---|---|---|
| | 690 | | | | | 695 | | | | | 700 | | | | |

| Val | Gln | Arg | Arg | Asn | Gln | Leu | His | Asp | Leu | Arg | Phe | Ala | Asp | Ile | Asp |
|---|---|---|---|---|---|---|---|---|---|---|---|---|---|---|---|
| 705 | | | | | 710 | | | | | 715 | | | | | 720 |

| Thr | Val | Ile | His | Ala | Asp | Ala | Asn | Ala | Ala | Met | Phe | Ala | Gly | Leu | Gly |
|---|---|---|---|---|---|---|---|---|---|---|---|---|---|---|---|
| | | | | 725 | | | | | 730 | | | | | 735 | |

| Ala | Phe | Phe | Glu | Gly | Met | Gly | Asp | Leu | Gly | Arg | Ala | Val | Gly | Lys | Val |
|---|---|---|---|---|---|---|---|---|---|---|---|---|---|---|---|
| | | | | 740 | | | | | 745 | | | | | 750 | |

| Val | Met | Gly | Ile | Val | Gly | Gly | Val | Val | Ser | Ala | Val | Ser | Gly | Val | Ser |
|---|---|---|---|---|---|---|---|---|---|---|---|---|---|---|---|
| | | 755 | | | | | 760 | | | | | 765 | | | |

| Ser | Phe | Met | Ser | Asn | Pro | Phe | Gly | Ala | Leu | Ala | Val | Gly | Leu | Leu | Val |
|---|---|---|---|---|---|---|---|---|---|---|---|---|---|---|---|
| 770 | | | | | 775 | | | | | 780 | | | | | |

| Leu | Ala | Gly | Leu | Ala | Ala | Ala | Phe | Phe | Ala | Phe | Arg | Tyr | Val | Met | Arg |
|---|---|---|---|---|---|---|---|---|---|---|---|---|---|---|---|
| 785 | | | | | 790 | | | | | 795 | | | | | 800 |

| Leu | Gln | Ser | Asn | Pro | Met | Lys | Ala | Leu | Tyr | Pro | Leu | Thr | Thr | Lys | Glu |
|---|---|---|---|---|---|---|---|---|---|---|---|---|---|---|---|
| | | | | 805 | | | | | 810 | | | | | 815 | |

| Leu | Lys | Asn | Pro | Thr | Asn | Pro | Asp | Ala | Ser | Gly | Glu | Gly | Glu | Glu | Gly |
|---|---|---|---|---|---|---|---|---|---|---|---|---|---|---|---|
| | | | 820 | | | | | 825 | | | | | 830 | | |

| Gly | Asp | Phe | Asp | Glu | Ala | Lys | Leu | Ala | Glu | Ala | Arg | Glu | Met | Ile | Arg |
|---|---|---|---|---|---|---|---|---|---|---|---|---|---|---|---|
| | | 835 | | | | | 840 | | | | | 845 | | | |

| Tyr | Met | Ala | Leu | Val | Ser | Ala | Met | Glu | Arg | Thr | Glu | His | Lys | Ala | Lys |
|---|---|---|---|---|---|---|---|---|---|---|---|---|---|---|---|
| | 850 | | | | | 855 | | | | | 860 | | | | |

| Lys | Lys | Gly | Thr | Ser | Ala | Leu | Leu | Ser | Ala | Lys | Val | Thr | Asp | Met | Val |
|---|---|---|---|---|---|---|---|---|---|---|---|---|---|---|---|
| 865 | | | | | 870 | | | | | 875 | | | | | 880 |

| Met | Arg | Lys | Arg | Arg | Asn | Thr | Asn | Tyr | Thr | Gln | Val | Pro | Asn | Lys | Asp |
|---|---|---|---|---|---|---|---|---|---|---|---|---|---|---|---|
| | | | | 885 | | | | | 890 | | | | | 895 | |

| Gly | Asp | Ala | Asp | Glu | Asp | Leu |
|---|---|---|---|---|---|---|
| | | | 900 | | | |

<210> SEQ ID NO 29
<211> LENGTH: 1800
<212> TYPE: DNA
<213> ORGANISM: Herpes Simplex Virus-1

<400> SEQUENCE: 29

```
agggcgcttg gtcgggaggc cgcatcgaac gcacaccccc atccggtggt ccgtgtggag      60
gtcgttttca tgcccggtct cgctttgtcg ggaacgctag ccggtccctc gcgagggga     120
ggcgtcgggc atggcccgg ggcggtgggg ccttgccgtg gtcctgtgga gcctgttgtg     180
gctcggggcg ggggtggccg gggctcgga aactgcctcc accggcccca cgatcaccgc     240
gggagcggtg acgaacgcga gcgaggcccc acatcggggg tccccggggt cagccgccag     300
ccccggaagtc accccacat cgaccccaaa ccccaacaat gtcacacaaa acaaaaccac     360
cccaccgag ccggccagcc cccaacaac ccccaagccc acctccacgc ccaaaagccc     420
```

```
cccacgtcc accccccgacc ccaaacccaa gaacaacacc accccccgcca agtcgggccg    480 cccactaaa ccccccgggc cgtgtggtg cgaccgccgc gacccattgg cccggtacgg      540
ctcgtgggtg cagatccgat gccggttttg gaattccacc cgcatggagt tccgcctcca   600
gatatggcgt tactccatgg gtccgtcccc cccaatcgct ccggctcccg acctagagga   660
ggtcctgacg aacatcaccg ccccacccgg gggactcctg gtgtacgaca gcgcccccaa   720
cctgacggac ccccacgtgc tctgggcgga ggggccggc ccgggcgccg acctccgtt    780 gtattctgtc accgggccgc tgccgaccca gcggctgatt atcggcgagg tgacgcccgc    840
gacccaggga atgtattact tggcctgggg ccggatggac agcccgcacg agtacgggac    900
gtgggtgcgc gtccgcatgt tccgcccccc gtctctgacc ctccagcccc acgcggtgat   960
ggagggtcag ccgttcaagg cgacgtgcac ggccgccgcc tactacccgc gtaaccccgt  1020
ggagtttgtc tggttcgagg acgaccgcca ggtgtttaac ccgggccaga tcgacacgca  1080
gacgcacgag cacccccgacg ggttcaccac agtctctacc gtgacctccg aggctgtcgg  1140
cggccaggtc ccccgcgga ccttcacctg ccagatgacg tggcaccgcg actccgtgac   1200
gttctcgcga cgcaatgcca ccgggctggc cctggtgctg ccgcggccaa ccatcaccat   1260
ggaatttggg gtccggcatg tggtctgcac ggccggctgc gtccccgagg gcgtgacgtt   1320
tgcctggttc ctgggggacg acccctcacc ggcggctaag tcggccgtta cggcccagga   1380
gtcgtgcgac caccccgggc tggctacggt ccggtccacc ctgcccattt cgtacgacta   1440
cagcgagtac atctgtcggt tgaccggata tccggccggg attccgttc tagagcacca   1500 cggcagtcac cagccccccac ccagggaccc caccgagcgg caggtgatcg aggcgatcga   1560
gtgggtgggg attggaatcg gggttctcgc ggcgggggtc ctggtcgtaa cggcaatcgt   1620
gtacgtcgtc cgcacatcac agtcgcggca gcgtcatcgg cggtaacgcg agaccccccc   1680 gttaccttt taatatctat atagtttggt ccccccctcta tcccgcccac cgctgggcgc   1740
tataaagccg ccaccctctc ttccctcagg tcatccttgg tcgatcccga acgacacacg   1800
```

<210> SEQ ID NO 30
<211> LENGTH: 511
<212> TYPE: PRT
<213> ORGANISM: Herpes Simplex Virus-1

<400> SEQUENCE: 30

```
Met Ala Pro Gly Arg Val Gly Leu Ala Val Val Leu Trp Gly Leu Leu
1               5                   10                  15

Trp Leu Gly Ala Gly Val Ala Gly Gly Ser Glu Thr Ala Ser Thr Gly
            20                  25                  30

Pro Thr Ile Thr Ala Gly Ala Val Thr Asn Ala Ser Glu Ala Pro Thr
        35                  40                  45

Ser Gly Ser Pro Gly Ser Ala Ala Ser Pro Glu Val Thr Pro Thr Ser
    50                  55                  60

Thr Pro Asn Pro Asn Asn Val Thr Gln Asn Lys Thr Thr Pro Thr Glu
65                  70                  75                  80

Pro Ala Ser Pro Pro Thr Thr Pro Lys Pro Thr Ser Thr Pro Lys Ser
                85                  90                  95

Pro Pro Thr Ser Thr Pro Asp Pro Lys Pro Lys Asn Asn Thr Thr Pro
            100                 105                 110

Ala Lys Ser Gly Arg Pro Thr Lys Pro Pro Gly Pro Val Trp Cys Asp
        115                 120                 125

Arg Arg Asp Pro Leu Ala Arg Tyr Gly Ser Arg Val Gln Ile Arg Cys
```

130                 135                 140
Arg Phe Arg Asn Ser Thr Arg Met Glu Phe Arg Leu Gln Ile Trp Arg
145                 150                 155                 160

Tyr Ser Met Gly Pro Ser Pro Ile Ala Pro Ala Pro Asp Leu Glu
                165                 170                 175

Glu Val Leu Thr Asn Ile Thr Ala Pro Pro Gly Gly Leu Leu Val Tyr
                180                 185                 190

Asp Ser Ala Pro Asn Leu Thr Asp Pro His Val Leu Trp Ala Glu Gly
                195                 200                 205

Ala Gly Pro Gly Ala Asp Pro Pro Leu Tyr Ser Val Thr Gly Pro Leu
            210                 215                 220

Pro Thr Gln Arg Leu Ile Ile Gly Glu Val Thr Pro Ala Thr Gln Gly
225                 230                 235                 240

Met Tyr Tyr Leu Ala Trp Gly Arg Met Asp Ser Pro His Glu Tyr Gly
                245                 250                 255

Thr Trp Val Arg Val Arg Met Phe Arg Pro Pro Ser Leu Thr Leu Gln
                260                 265                 270

Pro His Ala Val Met Glu Gly Gln Pro Phe Lys Ala Thr Cys Thr Ala
            275                 280                 285

Ala Ala Tyr Tyr Pro Arg Asn Pro Val Glu Phe Asp Trp Phe Glu Asp
290                 295                 300

Asp Arg Gln Val Phe Asn Pro Gly Gln Ile Asp Thr Gln Thr His Glu
305                 310                 315                 320

His Pro Asp Gly Phe Thr Thr Val Ser Thr Val Thr Ser Glu Ala Val
                325                 330                 335

Gly Gly Gln Val Pro Pro Arg Thr Phe Thr Cys Gln Met Thr Trp His
            340                 345                 350

Arg Asp Ser Val Thr Phe Ser Arg Arg Asn Ala Thr Gly Leu Ala Leu
                355                 360                 365

Val Leu Pro Arg Pro Thr Ile Thr Met Glu Phe Gly Val Arg His Val
            370                 375                 380

Val Cys Thr Ala Gly Cys Val Pro Glu Gly Val Thr Phe Ala Trp Phe
385                 390                 395                 400

Leu Gly Asp Asp Pro Ser Pro Ala Ala Lys Ser Ala Val Thr Ala Gln
                405                 410                 415

Glu Ser Cys Asp His Pro Gly Leu Ala Thr Val Arg Ser Thr Leu Pro
            420                 425                 430

Ile Ser Tyr Asp Tyr Ser Glu Tyr Ile Cys Arg Leu Thr Gly Tyr Pro
            435                 440                 445

Ala Gly Ile Pro Val Leu Glu His His Gly Ser His Gln Pro Pro Pro
450                 455                 460

Arg Asp Pro Thr Glu Arg Gln Val Ile Glu Ala Ile Glu Trp Val Gly
465                 470                 475                 480

Ile Gly Ile Gly Val Leu Ala Ala Gly Val Leu Val Val Thr Ala Ile
                485                 490                 495

Val Tyr Val Val Arg Thr Ser Gln Ser Arg Gln Arg His Arg Arg
                500                 505                 510

<210> SEQ ID NO 31
<211> LENGTH: 1282
<212> TYPE: DNA
<213> ORGANISM: Homo sapiens

<400> SEQUENCE: 31

```
aagccaccca gcctatgcat ccgctcctca atcctctcct gttggcactg ggcctcatgg      60
cgcttttgtt gaccacggtc attgctctca cttgccttgg cggctttgcc tccccaggcc    120
ctgtgcctcc ctctacagcc ctcagggagc tcattgagga gctggtcaac atcacccaga    180
accagaaggc tccgctctgc aatggcagca tggtatggag catcaacctg acagctggca    240
tgtactgtgc agccctggaa tcctgatca acgtgtcagg ctgcagtgcc atcgagaaga     300
cccagaggat gctgagcgga ttctgcccgc acaaggtctc agctgggcag ttttccagct    360
tgcatgtccg agacaccaaa atcgaggtgg cccagtttgt aaaggacctg ctcttacatt    420
taaagaaact ttttcgcgag ggacagttca actgaaactt cgaaagcatc attatttgca    480
gagacaggac ctgactattg aagttgcaga ttcattttc tttctgatgt caaaaatgtc     540
ttgggtaggc gggaaggagg gttagggagg ggtaaaattc cttagcttag acctcagcct    600
gtgctgcccg tcttcagcct agccgacctc agccttcccc ttgcccaggg ctcagcctgg    660
tgggcctcct ctgtccaggg ccctgagctc ggtggaccca gggatgacat gtccctacac    720
ccctcccctg ccctagagca cactgtagca ttacagtggg tgccccctt gccagacatg     780
tggtgggaca gggacccact tcacacacag gcaactgagg cagacagcag ctcaggcaca    840
cttcttcttg gtcttattta ttattgtgtg ttatttaaat gagtgtgttt gtcaccgttg    900
gggattgggg aagactgtgg ctgctagcac ttggagccaa gggttcagag actcagggcc    960
ccagcactaa agcagtggac accaggagtc cctggtaata agtactgtgt acagaattct   1020
gctacctcac tggggtcctg ggcctcgga gcctcatccg aggcagggtc aggagagggg    1080
cagaacagcc gctcctgtct gccagccagc agccagctct cagccaacga gtaatttatt   1140
gttttccctt gtatttaaat attaaatatg ttagcaaaga gttaatatat agaagggtac   1200
cttgaacact gggggagggg acattgaaca agttgtttca ttgactatca aactgaagcc   1260
agaaataaag ttggtgacag at                                             1282
```

<210> SEQ ID NO 32
<211> LENGTH: 146
<212> TYPE: PRT
<213> ORGANISM: Homo sapiens

<400> SEQUENCE: 32

```
Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140
```

<210> SEQ ID NO 33
<211> LENGTH: 1376
<212> TYPE: DNA
<213> ORGANISM: Homo sapiens

<400> SEQUENCE: 33

```
gtaagaacac tctcgtgagt ctaacggtct tccggatgaa ggctatttga agtcgccata    60
acctggtcag aagtgtgcct gtcggcgggg agagaggcaa tatcaaggtt ttaaatctcg   120
gagaaatggc tttcgtttgc ttggctatcg gatgcttata acctttctg ataagcacaa   180
catttggctg tacttcatct tcagacaccg agataaaagt taaccctcct caggattttg   240
agatagtgga tcccggatac ttaggttatc tctatttgca atggcaaccc ccactgtctc   300
tggatcattt taaggaatgc acagtggaat atgaactaaa ataccgaaac attggtagtg   360
aaacatggaa gaccatcatt actaagaatc tacattacaa agatgggttt gatcttaaca   420
agggcattga agcgaagata cacacgcttt taccatggca atgcacaaat ggatcagaag   480
ttcaaagttc ctgggcagaa actacttatt ggatatcacc acaaggaatt ccagaaacta   540
aagttcagga tatggattgc gtatattaca attggcaata tttactctgt tcttggaaac   600
ctggcatagg tgtacttctt gataccaatt acaacttgtt ttactggtat gagggcttgg   660
atcatgcatt acagtgtgtt gattacatca aggctgatgg acaaaatata ggatgcagat   720
ttccctattt ggaggcatca gactataaag atttctatat ttgtgttaat ggatcatcag   780
agaacaagcc tatcagatcc agttatttca ctttttcagct tcaaaatata gttaaacctt   840
tgccgccagt ctatcttact tttactcggg agagttcatg tgaaattaag ctgaaatgga   900
gcatacccttt gggaccctatt ccagcaaggt gttttgatta tgaaattgag atcagagaag   960
atgatactac cttggtgact gctacagttg aaaatgaaac atacaccttg aaaacaacaa  1020
atgaaacccg acaattatgc tttgtagtaa gaagcaaagt gaatatttat tgctcagatg  1080
acggaatttg gagtgagtgg agtgataaac aatgctggga aggtgaagac ctatcgaaga  1140
aaactttgct acgtttctgg ctaccatttg gtttcatctt aatattagtt atatttgtaa  1200
ccggtctgct tttgcgtaag ccaaacacct acccaaaaat gattccagaa ttttttctgtg  1260
atacatgaag actttccata tcaagagaca tggtattgac tcaacagttt ccagtcatgg  1320
ccaaatgttc aatatgagtc tcaataaact gaattttttct tgcgaatgtt gaaaaa      1376
```

<210> SEQ ID NO 34
<211> LENGTH: 380
<212> TYPE: PRT
<213> ORGANISM: Homo sapiens

<400> SEQUENCE: 34

```
Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
        50                  55                  60

Cys Thr Val Glu Tyr Glu Leu Lys Tyr Arg Asn Ile Gly Ser Glu Thr
65                  70                  75                  80
```

```
Trp Lys Thr Ile Ile Thr Lys Asn Leu His Tyr Lys Asp Gly Phe Asp
                85                  90                  95
Leu Asn Lys Gly Ile Glu Ala Lys Ile His Thr Leu Leu Pro Trp Gln
            100                 105                 110
Cys Thr Asn Gly Ser Glu Val Gln Ser Ser Trp Ala Glu Thr Thr Tyr
        115                 120                 125
Trp Ile Ser Pro Gln Gly Ile Pro Glu Thr Lys Val Gln Asp Met Asp
    130                 135                 140
Cys Val Tyr Tyr Asn Trp Gln Tyr Leu Leu Cys Ser Trp Lys Pro Gly
145                 150                 155                 160
Ile Gly Val Leu Leu Asp Thr Asn Tyr Asn Leu Phe Tyr Trp Tyr Glu
                165                 170                 175
Gly Leu Asp His Ala Leu Gln Cys Val Asp Tyr Ile Lys Ala Asp Gly
            180                 185                 190
Gln Asn Ile Gly Cys Arg Phe Pro Tyr Leu Glu Ala Ser Asp Tyr Lys
        195                 200                 205
Asp Phe Tyr Ile Cys Val Asn Gly Ser Ser Glu Asn Lys Pro Ile Arg
    210                 215                 220
Ser Ser Tyr Phe Thr Phe Gln Leu Gln Asn Ile Val Lys Pro Leu Pro
225                 230                 235                 240
Pro Val Tyr Leu Thr Phe Thr Arg Glu Ser Ser Cys Glu Ile Lys Leu
                245                 250                 255
Lys Trp Ser Ile Pro Leu Gly Pro Ile Pro Ala Arg Cys Phe Asp Tyr
            260                 265                 270
Glu Ile Glu Ile Arg Glu Asp Asp Thr Thr Leu Val Thr Ala Thr Val
        275                 280                 285
Glu Asn Glu Thr Tyr Thr Leu Lys Thr Thr Asn Glu Thr Arg Gln Leu
    290                 295                 300
Cys Phe Val Val Arg Ser Lys Val Asn Ile Tyr Cys Ser Asp Asp Gly
305                 310                 315                 320
Ile Trp Ser Glu Trp Ser Asp Lys Gln Cys Trp Gly Glu Asp Leu
                325                 330                 335
Ser Lys Lys Thr Leu Leu Arg Phe Trp Leu Pro Phe Gly Phe Ile Leu
            340                 345                 350
Ile Leu Val Ile Phe Val Thr Gly Leu Leu Leu Arg Lys Pro Asn Thr
        355                 360                 365
Tyr Pro Lys Met Ile Pro Glu Phe Phe Cys Asp Thr
    370                 375                 380

<210> SEQ ID NO 35
<211> LENGTH: 2685
<212> TYPE: DNA
<213> ORGANISM: Herpes Simplex Virus-1

<400> SEQUENCE: 35
atgcgccagg gcgccccgc gcgggggcgc cggtggttcg tcgtatgggc gctcttgggg      60
ttgacgctgg gggtcctggt ggcgtcggcg gctccgagtt ccccggcac gcctggggtc     120 gcggccgcga cccaggcggc gaacggggc cctgccactc cggcgccgcc cgccctggc     180 gccccccaa cggggaccc gccaaagccg ccgcgccccg ccggcgacaa cgcgaccgtc     240
gccgcgggcc acgccaccct gcgcgagcac ctgcgggaca tcaaggcgga gaacaccgat     300
gcaaactttt acgtgtgccc accccccacg ggcgccacgg tggtgcagtt cgagcagccg     360
cgccgctgcc cgacccggcc cgagggtcag aactacacgg agggcatcgc ggtggtcttc     420
```

```
aaggagaaca tcgccccgta caagttcaag gccaccatgt actacaaaga cgtcaccgtt    480
tcgcaggtgt ggttcggcca ccgctactcc cagtttatgg ggatctttga ggaccgcgcc    540
cccgtcccct tcgaggaggt gatcgacaag atcaacgcca aggggggtctg tcggtccacg   600 gccaagtacg tgcgcaacaa cctggagacc accgcgtttc accgggacga ccacgagacc    660
gacatggagc tgaaaccggc caacgccgcg acccgcacga gccggggctg gcacaccacc    720
gacctcaagt acaacccctc gcgggtggag gcgttccacc ggtacgggac gacggtaaac    780
tgcatcgtcg aggaggtgga cgcgcgctcg gtgtacccgt acgacgagtt tgtgttggcg    840
actggcgact ttgtgtacat gtccccgttt tacggctacc gggaggggtc gcacaccgaa    900
cacaccagct acgccgccga ccgcttcaag caggtcgacg gcttctacgc gcgcgacctc    960
accaccaagg cccgggccac ggcgccgacc accggaacc tgctcacgac ccccaagttc      1020
accgtggcct gggactgggt gccaaagcgc ccgtcggtct gcaccatgac caagtggcag    1080
gaggtggacg agatgctgcg ctccgagtac ggcggctcct tccgattctc ttccgacgcc    1140
atatccacca ccttcaccac caacctgacc gagtacccgc tctcgcgcgt ggacctgggg    1200
gactgcatcg gcaaggacgc ccgcgacgcc atggaccgca tcttcgcccg caggtacaac    1260
gcgacgcaca tcaaggtggg ccagccgcag tactacctgg ccaatggggg ctttctgatc    1320
gcgtaccagc cccttctcag caacacgctc gcggagctgt acgtgcggga cacctccgc     1380 gagcagagcc gcaagccccc aaaccccacg ccccgccgc ccggggccag cgccaacgcg      1440
tccgtggagc gcatcaagac cacctcctcc atcgagttcg ccaggctgca gtttacgtac    1500
aaccacatac agcgccatgt caacgatatg ttgggccgcg ttgccatcgc gtggtgcgag    1560
ctgcagaatc acgagctgac cctgtggaac gaggcccgca agctgaaccc caacgccatc    1620
gcctcggcca ccgtgggccg gcgggtgagc gcgcggatgc tcggcgacgt gatggccgtc    1680
tccacgtgcg tgccggtcgc cgcggacaac gtgatcgtcc aaaactcgat gcgcatcagc    1740
tcgcggcccg gggcctgcta cagccgcccc ctggtcagct ttcggtacga agaccagggc    1800
ccgttggtcg agggggcagct gggggagaac aacgagctgc ggctgacgcg cgatgcgatc    1860
gagccgtgca ccgtgggaca ccggcgctac ttcacccttcg gtgggggcta cgtgtacttc    1920
gaggagtacg cgtactccca ccagctgagc cgcgccgaca tcaccaccgt cagcaccttc    1980
atcgacctca acatcaccat gctggaggat cacgagtttg tcccccctgga ggtgtacacc    2040 cgccacgaga tcaaggacag cggcctgctg gactacacgg aggtccagcg ccgcaaccag    2100
ctgcacgacc tgcgcttcgc cgacatcgac acggtcatcc acgccgacgc caacgccgcc    2160
atgtttgcgg gcctgggcgc gttcttcgag gggatgggcg acctggggcg cgcggtcggc    2220
aaggtggtga tgggcatcgt gggcggcgtg gtatcggccg tgtcgggcgt gtcctccttc    2280
atgtccaacc ccttgggggc gctggccgtg gtctgttgg tcctggccgg cctggcggcg     2340
gccttcttcg ccttcgcta cgtcatgcgc ctgcagagca accccatgaa ggccctgtac    2400
ccgctaacca ccaaggagct caagaacccc accaacccgg acgcgtccgg ggagggcgag    2460
gagggcggcg actttgacga ggccaagcta gccgaggccc gggagatgat acggtacatg    2520
gccctggtgt ctgccatgga gcgcacggaa cacaaggcca agaagaaggg cacgagcgcg    2580
ctgctcagcg ccaaggtcac cgacatggtc atgcgcaagc gccgcaacac caactacacc    2640
caagttccca caaagacgg tgacgccgac gaggacgacc tgtga                    2685
```

<210> SEQ ID NO 36

<211> LENGTH: 894
<212> TYPE: PRT
<213> ORGANISM: Herpes Simplex Virus-1

<400> SEQUENCE: 36

Met Arg Gln Gly Ala Pro Ala Arg Gly Arg Arg Trp Phe Val Val Trp
1 5 10 15

Ala Leu Leu Gly Leu Thr Leu Gly Val Leu Val Ala Ser Ala Ala Pro
20 25 30

Ser Ser Pro Gly Thr Pro Gly Val Ala Ala Ala Thr Gln Ala Ala Asn
35 40 45

Gly Gly Pro Ala Thr Pro Ala Pro Pro Ala Pro Gly Ala Pro Pro Thr
50 55 60

Gly Asp Pro Pro Lys Pro Pro Arg Pro Ala Gly Asp Asn Ala Thr Val
65 70 75 80

Ala Ala Gly His Ala Thr Leu Arg Glu His Leu Arg Asp Ile Lys Ala
85 90 95

Glu Asn Thr Asp Ala Asn Phe Tyr Val Cys Pro Pro Pro Thr Gly Ala
100 105 110

Thr Val Val Gln Phe Glu Gln Pro Arg Arg Cys Pro Thr Arg Pro Glu
115 120 125

Gly Gln Asn Tyr Thr Glu Gly Ile Ala Val Val Phe Lys Glu Asn Ile
130 135 140

Ala Pro Tyr Lys Phe Lys Ala Thr Met Tyr Tyr Lys Asp Val Thr Val
145 150 155 160

Ser Gln Val Trp Phe Gly His Arg Tyr Ser Gln Phe Met Gly Ile Phe
165 170 175

Glu Asp Arg Ala Pro Val Pro Phe Glu Glu Val Ile Asp Lys Ile Asn
180 185 190

Ala Lys Gly Val Cys Arg Ser Thr Ala Lys Tyr Val Arg Asn Asn Leu
195 200 205

Glu Thr Thr Ala Phe His Arg Asp Asp His Glu Thr Asp Met Glu Leu
210 215 220

Lys Pro Ala Asn Ala Ala Thr Arg Thr Ser Arg Gly Trp His Thr Thr
225 230 235 240

Asp Leu Lys Tyr Asn Pro Ser Arg Val Glu Ala Phe His Arg Tyr Gly
245 250 255

Thr Thr Val Asn Cys Ile Val Glu Glu Val Asp Ala Arg Ser Val Tyr
260 265 270

Pro Tyr Asp Glu Phe Val Leu Ala Thr Gly Asp Phe Val Tyr Met Ser
275 280 285

Pro Phe Tyr Gly Tyr Arg Glu Gly Ser His Thr Glu His Thr Ser Tyr
290 295 300

Ala Ala Asp Arg Phe Lys Gln Val Asp Gly Phe Tyr Ala Arg Asp Leu
305 310 315 320

Thr Thr Lys Ala Arg Ala Thr Ala Pro Thr Thr Arg Asn Leu Leu Thr
325 330 335

Thr Pro Lys Phe Thr Val Ala Trp Asp Trp Val Pro Lys Arg Pro Ser
340 345 350

Val Cys Thr Met Thr Lys Trp Gln Glu Val Asp Glu Met Leu Arg Ser
355 360 365

Glu Tyr Gly Gly Ser Phe Arg Phe Ser Ser Asp Ala Ile Ser Thr Thr
370 375 380

Phe Thr Thr Asn Leu Thr Glu Tyr Pro Leu Ser Arg Val Asp Leu Gly

```
            385                 390                 395                 400
        Asp Cys Ile Gly Lys Asp Ala Arg Asp Ala Met Asp Arg Ile Phe Ala
                        405                 410                 415

Arg Arg Tyr Asn Ala Thr His Ile Lys Val Gly Gln Pro Gln Tyr Tyr
                        420                 425                 430

Leu Ala Asn Gly Gly Phe Leu Ile Ala Tyr Gln Pro Leu Leu Ser Asn
                        435                 440                 445

Thr Leu Ala Glu Leu Tyr Val Arg Glu His Leu Arg Glu Gln Ser Arg
                    450                 455                 460

Lys Pro Pro Asn Pro Thr Pro Pro Pro Gly Ala Ser Ala Asn Ala
        465                 470                 475                 480

Ser Val Glu Arg Ile Lys Thr Thr Ser Ser Ile Glu Phe Ala Arg Leu
                        485                 490                 495

Gln Phe Thr Tyr Asn His Ile Gln Arg His Val Asn Asp Met Leu Gly
                        500                 505                 510

Arg Val Ala Ile Ala Trp Cys Glu Leu Gln Asn His Glu Leu Thr Leu
                        515                 520                 525

Trp Asn Glu Ala Arg Lys Leu Asn Pro Asn Ala Ile Ala Ser Ala Thr
                    530                 535                 540

Val Gly Arg Arg Val Ser Ala Arg Met Leu Gly Asp Val Met Ala Val
        545                 550                 555                 560

Ser Thr Cys Val Pro Val Ala Ala Asp Asn Val Ile Val Gln Asn Ser
                        565                 570                 575

Met Arg Ile Ser Ser Arg Pro Gly Ala Cys Tyr Ser Arg Pro Leu Val
                        580                 585                 590

Ser Phe Arg Tyr Glu Asp Gln Gly Pro Leu Val Glu Gly Gln Leu Gly
                    595                 600                 605

Glu Asn Asn Glu Leu Arg Leu Thr Arg Asp Ala Ile Glu Pro Cys Thr
                        610                 615                 620

Val Gly His Arg Arg Tyr Phe Thr Phe Gly Gly Tyr Val Tyr Phe
        625                 630                 635                 640

Glu Glu Tyr Ala Tyr Ser His Gln Leu Ser Arg Ala Asp Ile Thr Thr
                        645                 650                 655

Val Ser Thr Phe Ile Asp Leu Asn Ile Thr Met Leu Glu Asp His Glu
                        660                 665                 670

Phe Val Pro Leu Glu Val Tyr Thr Arg His Glu Ile Lys Asp Ser Gly
                        675                 680                 685

Leu Leu Asp Tyr Thr Glu Val Gln Arg Arg Asn Gln Leu His Asp Leu
                        690                 695                 700

Arg Phe Ala Asp Ile Asp Thr Val Ile His Ala Asp Ala Asn Ala Ala
        705                 710                 715                 720

Met Phe Ala Gly Leu Gly Ala Phe Phe Glu Met Gly Asp Leu Gly
                        725                 730                 735

Arg Ala Val Gly Lys Val Val Met Gly Ile Val Gly Val Val Ser
                        740                 745                 750

Ala Val Ser Gly Val Ser Ser Phe Met Ser Asn Pro Phe Gly Ala Leu
                        755                 760                 765

Ala Val Gly Leu Leu Val Leu Ala Gly Leu Ala Ala Phe Phe Ala
                        770                 775                 780

Phe Arg Tyr Val Met Arg Leu Gln Ser Asn Pro Met Lys Ala Leu Tyr
        785                 790                 795                 800

Pro Leu Thr Thr Lys Glu Leu Lys Asn Pro Thr Asn Pro Asp Ala Ser
                        805                 810                 815
```

Gly Glu Gly Glu Glu Gly Gly Asp Phe Asp Glu Ala Lys Leu Ala Glu
            820                 825                 830

Ala Arg Glu Met Ile Arg Tyr Met Ala Leu Val Ser Ala Met Glu Arg
        835                 840                 845

Thr Glu His Lys Ala Lys Lys Gly Thr Ser Ala Leu Leu Ser Ala
    850                 855                 860

Lys Val Thr Asp Met Val Met Arg Lys Arg Arg Asn Thr Asn Tyr Thr
865                 870                 875                 880

Gln Val Pro Asn Lys Asp Gly Asp Ala Asp Glu Asp Asp Leu
                885                 890

<210> SEQ ID NO 37
<211> LENGTH: 1626
<212> TYPE: DNA
<213> ORGANISM: Herpes Simplex Virus-1

<400> SEQUENCE: 37

```
atggcgcttt tgttgaccac ggtcattgct ctcacttgcc ttggcggctt tgcctcccca        60
ggccctgtgc ctccctctac agccctcagg gagctcattg aggagctggt caacatcacc       120
cagaaccaga aggctccgct ctgcaatggc agcatggtat ggagcatcaa cctgacagct       180
ggcatgtact gtgcagccct ggaatccctg atcaacgtgt caggctgcag tgccatcgag       240
aagacccaga ggatgctgag cggattctgc ccgcacaagg tctcagctgg cagttttcc        300 agcttgcatg tccgagacac caaaatcgag gtggcccagt ttgtaaagga cctgctctta       360
catttaaaga aacttttcg cgagggacag ttcaacgaat ccacccgca tggagttccg        420 cctccagata tggcgttact ccatgggtcc gtcccccca atcgctccgg ctcccgacct        480
agaggaggtc ctgacgaaca tcaccgcccc accggggga ctcctggtgt acgacagcgc        540
ccccaacctg acggaccccc acgtgctctg gcggagggg gccggccggg cgccgaccc         600 tccgttgtat tctgtcaccg gccgctgcc gacccagcgg ctgattatcg gcgaggtgac        660
gcccgcgacc cagggaatgt attacttggc ctggggccgg atggacagcc gcacgagta        720 cgggacgtgg gtgcgcgtcc gcatgttccg cccccgtct ctgaccctcc agccccacgc        780
ggtgatggag ggtcagccgt tcaaggcgac gtgcacggcc gccgcctact accgcgtaa        840 cccgtggag tttgtctggt tcgaggacga ccgccaggtg tttaacccgg gccagatcga        900
cacgcagacg cacgagcacc ccgacgggtt caccacagtc tctaccgtga cctccgaggc        960
tgtcggcggc caggtccccc gcggaccctt cacctgccag atgacgtggc accgcgactc       1020
cgtgacgttc tcgcgacgca atgccaccgg gctggccctg gtgctgccgc ggccaaccat       1080
caccatggaa tttgggggtcc ggcatgtggt ctgcacggcc ggctgcgtcc ccagggcgt       1140 gacgtttgcc tggttcctgg ggacgaccc ctcaccggcg gctaagtcgg ccgttacggc       1200
ccaggagtcg tgcgaccacc ccgggctggc tacggtccgg tccacccgtgc ccatttcgta       1260 cgactacagc gagtacatct gtcggttgac cggatatccg gccgggattc ccgttctaga       1320
gcaccacggc agtcaccagc ccccaccag ggaccccacc gagcggcagg tgatcgaggc       1380
gatcgagtgg gtgggattg aatcgggggt tctcgcggcg ggggtcctgg tcgtaacggc       1440
aatcgtgtac gtcgtccgca catcacagtc gcggcagcgt catcggcggt aacgcgagac       1500
ccccccgtta cctttttaat atctatatag tttggtcccc cctctatccc gccaccgct        1560 gggcgctata aagccgccac cctctcttcc ctcaggtcat ccttggtcga tcccgaacga       1620
cacacg                                                                1626
```

-continued

```
<210> SEQ ID NO 38
<211> LENGTH: 497
<212> TYPE: PRT
<213> ORGANISM: Herpes Simplex Virus-1

<400> SEQUENCE: 38

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Gln Phe Asn Glu Phe Ser Thr Arg Met Glu Phe Arg Leu Gln Ile
    130                 135                 140

Trp Arg Tyr Ser Met Gly Pro Ser Pro Ile Ala Pro Ala Pro Asp
145                 150                 155                 160

Leu Glu Glu Val Leu Thr Asn Ile Thr Ala Pro Pro Gly Gly Leu Leu
                165                 170                 175

Val Tyr Asp Ser Ala Pro Asn Leu Thr Asp Pro His Val Leu Trp Ala
            180                 185                 190

Glu Gly Ala Gly Pro Gly Ala Asp Pro Pro Leu Tyr Ser Val Thr Gly
        195                 200                 205

Pro Leu Pro Thr Gln Arg Leu Ile Ile Gly Glu Val Thr Pro Ala Thr
    210                 215                 220

Gln Gly Met Tyr Tyr Leu Ala Trp Gly Arg Met Asp Ser Pro His Glu
225                 230                 235                 240

Tyr Gly Thr Trp Val Arg Val Arg Met Phe Arg Pro Pro Ser Leu Thr
                245                 250                 255

Leu Gln Pro His Ala Val Met Glu Gly Gln Pro Phe Lys Ala Thr Cys
            260                 265                 270

Thr Ala Ala Ala Tyr Tyr Pro Arg Asn Pro Val Glu Phe Asp Trp Phe
        275                 280                 285

Glu Asp Asp Arg Gln Val Phe Asn Pro Gly Gln Ile Asp Thr Gln Thr
    290                 295                 300

His Glu His Pro Asp Gly Phe Thr Thr Val Ser Thr Val Thr Ser Glu
305                 310                 315                 320

Ala Val Gly Gly Gln Val Pro Pro Arg Thr Phe Thr Cys Gln Met Thr
                325                 330                 335

Trp His Arg Asp Ser Val Thr Phe Ser Arg Arg Asn Ala Thr Gly Leu
            340                 345                 350

Ala Leu Val Leu Pro Arg Pro Thr Ile Thr Met Glu Phe Gly Val Arg
        355                 360                 365

His Val Val Cys Thr Ala Gly Cys Val Pro Glu Gly Val Thr Phe Ala
```

```
                370             375              380
Trp Phe Leu Gly Asp Asp Pro Ser Pro Ala Ala Lys Ser Ala Val Thr
385                 390                 395                 400

Ala Gln Glu Ser Cys Asp His Pro Gly Leu Ala Thr Val Arg Ser Thr
            405                 410                 415

Leu Pro Ile Ser Tyr Asp Tyr Ser Glu Tyr Ile Cys Arg Leu Thr Gly
                420                 425                 430

Tyr Pro Ala Gly Ile Pro Val Leu Glu His His Gly Ser His Gln Pro
            435                 440                 445

Pro Pro Arg Asp Pro Thr Glu Arg Gln Val Ile Glu Ala Ile Glu Trp
        450                 455                 460

Val Gly Ile Gly Ile Gly Val Leu Ala Ala Gly Val Leu Val Val Thr
465                 470                 475                 480

Ala Ile Val Tyr Val Val Arg Thr Ser Gln Ser Arg Gln Arg His Arg
                485                 490                 495

Arg
```

<210> SEQ ID NO 39
<211> LENGTH: 1593
<212> TYPE: DNA
<213> ORGANISM: Herpes Simplex Virus-1

<400> SEQUENCE: 39

```
atggggggg  ctgccgccag  gttgggggcc  gtgattttgt  ttgtcgtcat  agtgggcctc     60
catgggtcc  gcggcaaata  tgccttggcg  gatgcctctc  tcaagatggc  cgaccccaat    120
cgctttcgcg  gcaaagacct  tccggtcctc  gagatggcgc  ttttgttgac  cacggtcatt    180
gctctcactt  gccttggcgg  ctttgcctcc  ccaggccctg  tgcctccctc  tacagccctc    240
agggagctca  ttgaggagct  ggtcaacatc  acccagaacc  agaaggctcc  gctctgcaat    300
ggcagcatgg  tatggagcat  caacctgaca  gctggcatgt  actgtgcagc  cctggaatcc    360
ctgatcaacg  tgtcaggctg  cagtgccatc  gagaagaccc  agaggatgct  gagcggattc    420
tgcccgcaca  aggtctcagc  tgggcagttt  ccagcttgc   atgtccgaga  caccaaaatc    480
gaggtggccc  agtttgtaaa  ggacctgctc  ttacatttaa  agaaactttt  tcgcgaggga    540
cagttcaacg  gtaccctgga  ccggctgacc  gaccctccgg  gggtccggcg  cgtgtaccac    600
atccaggcgg  gcctaccgga  cccgttccag  ccccccagcc  tcccgatcac  ggttactac     660
gccgtgttgg  agcgcgcctg  ccgcagcgtg  ctcctaaacg  caccgtcgga  ggccccccag    720
attgtccgcg  gggcctccga  agacgtccgg  aaacaaccct  acaacctgac  catcgcttgg    780
tttcggatgg  gaggcaactg  tgctatcccc  atcacggtca  tggagtacac  cgaatgctcc    840
tacaacaagt  ctctgggggc  ctgtcccatc  cgaacgcagc  ccgctggaa   ctactatgac    900
agcttcagcg  ccgtcagcga  ggataacctg  ggttcctga   tgcacgcccc  cgcgtttgag    960
accgccggca  cgtacctgcg  gctcgtgaag  ataaacgact  ggacggagat  tacacagttt   1020
atcctggagc  accgagccaa  gggctcctgt  aagtacgccc  ttccgctgcg  catcccccg    1080
tcagcctgcc  tctcccccca  ggcctaccag  caggggtga   cggtggacag  catcgggatg   1140
ctgccccgct  tcatccccga  gaaccagcgc  accgtcgccg  tatacagctt  gaagatcgcc   1200
gggtggcacg  ggcccaaggc  cccatacacg  agcaccctgc  tgccccggga  gctgtccgag   1260
acccccaacg  ccacgcagcc  agaactcgcc  cggaagacc   ccgaggattc  ggccctcttg   1320
gaggaccccg  tggggacggt  ggtgccgcaa  atcccaccaa  actggcacat  accgtcgatc   1380
```

```
caggacgccg cgacgcctta ccatccccg gccaccccga acaacatggg cctgatcgcc    1440
ggcgcggtgg gcggcagtct cctggtagcc ctggtcattt gcggaattgt gtactggatg    1500
cgccgccgca ctcaaaaagc cccaaagcgc atacgcctcc cccacatccg ggaagacgac    1560
cagccgtcct cgcaccagcc cttgttttac tag                                 1593
```

<210> SEQ ID NO 40
<211> LENGTH: 530
<212> TYPE: PRT
<213> ORGANISM: Herpes Simplex Virus-1

<400> SEQUENCE: 40

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Glu Met Ala Leu Leu Leu Thr Thr Val Ile Ala Leu Thr Cys
    50                  55                  60

Leu Gly Gly Phe Ala Ser Pro Gly Pro Val Pro Pro Ser Thr Ala Leu
65                  70                  75                  80

Arg Glu Leu Ile Glu Glu Leu Val Asn Ile Thr Gln Asn Gln Lys Ala
                85                  90                  95

Pro Leu Cys Asn Gly Ser Met Val Trp Ser Ile Asn Leu Thr Ala Gly
            100                 105                 110

Met Tyr Cys Ala Ala Leu Glu Ser Leu Ile Asn Val Ser Gly Cys Ser
        115                 120                 125

Ala Ile Glu Lys Thr Gln Arg Met Leu Ser Gly Phe Cys Pro His Lys
    130                 135                 140

Val Ser Ala Gly Gln Phe Ser Ser Leu His Val Arg Asp Thr Lys Ile
145                 150                 155                 160

Glu Val Ala Gln Phe Val Lys Asp Leu Leu Leu His Leu Lys Lys Leu
                165                 170                 175

Phe Arg Glu Gly Gln Phe Asn Gly Thr Pro Arg Leu Thr Asp Pro
            180                 185                 190

Pro Gly Val Arg Arg Val Tyr His Ile Gln Ala Gly Leu Pro Asp Pro
        195                 200                 205

Phe Gln Pro Pro Ser Leu Pro Ile Thr Val Tyr Tyr Ala Val Leu Glu
    210                 215                 220

Arg Ala Cys Arg Ser Val Leu Leu Asn Ala Pro Ser Glu Ala Pro Gln
225                 230                 235                 240

Ile Val Arg Gly Ala Ser Glu Asp Val Arg Lys Gln Pro Tyr Asn Leu
                245                 250                 255

Thr Ile Ala Trp Phe Arg Met Gly Gly Asn Cys Ala Ile Pro Ile Thr
            260                 265                 270

Val Met Glu Tyr Thr Glu Cys Ser Tyr Asn Lys Ser Leu Gly Ala Cys
        275                 280                 285

Pro Ile Arg Thr Gln Pro Arg Trp Asn Tyr Tyr Asp Ser Phe Ser Ala
    290                 295                 300

Val Ser Glu Asp Asn Leu Gly Phe Leu Met His Ala Pro Ala Phe Glu
305                 310                 315                 320

Thr Ala Gly Thr Tyr Leu Arg Leu Val Lys Ile Asn Asp Trp Thr Glu
                325                 330                 335
```

```
Ile Thr Gln Phe Ile Leu Glu His Arg Ala Lys Gly Ser Cys Lys Tyr
            340                 345                 350

Ala Leu Pro Leu Arg Ile Pro Pro Ser Ala Cys Leu Ser Pro Gln Ala
        355                 360                 365

Tyr Gln Gln Gly Val Thr Val Asp Ser Ile Gly Met Leu Pro Arg Phe
    370                 375                 380

Ile Pro Glu Asn Gln Arg Thr Val Ala Val Tyr Ser Leu Lys Ile Ala
385                 390                 395                 400

Gly Trp His Gly Pro Lys Ala Pro Tyr Thr Ser Thr Leu Leu Pro Pro
                405                 410                 415

Glu Leu Ser Glu Thr Pro Asn Ala Thr Gln Pro Glu Leu Ala Pro Glu
            420                 425                 430

Asp Pro Glu Asp Ser Ala Leu Leu Glu Asp Pro Val Gly Thr Val Val
        435                 440                 445

Pro Gln Ile Pro Pro Asn Trp His Ile Pro Ser Ile Gln Asp Ala Ala
    450                 455                 460

Thr Pro Tyr His Pro Pro Ala Thr Pro Asn Asn Met Gly Leu Ile Ala
465                 470                 475                 480

Gly Ala Val Gly Gly Ser Leu Leu Val Ala Leu Val Ile Cys Gly Ile
                485                 490                 495

Val Tyr Trp Met Arg Arg Arg Thr Gln Lys Ala Pro Lys Arg Ile Arg
            500                 505                 510

Leu Pro His Ile Arg Glu Asp Asp Gln Pro Ser Ser His Gln Pro Leu
        515                 520                 525

Phe Tyr
    530

<210> SEQ ID NO 41
<211> LENGTH: 1416
<212> TYPE: DNA
<213> ORGANISM: Herpes Simplex Virus-1

<400> SEQUENCE: 41
atggcgcttt tgttgaccac ggtcattgct ctcacttgcc ttggcggctt tgcctcccca      60
ggccctgtgc ctccctctac agccctcagg gagctcattg aggagctggt caacatcacc     120
cagaaccaga aggctccgct ctgcaatggc agcatggtat ggagcatcaa cctgacagct     180
ggcatgtact gtgcagccct ggaatccctg atcaacgtgt caggctgcag tgccatcgag     240
aagacccaga ggatgctgag cggattctgc cgcacaaggt ctcagctggc agttttcc      300 agcttgcatg tccgagacac caaaatcgag gtggcccagt tgtaaagga cctgctctta     360 catttaaaga aactttttcg cgagggacag ttcaacggta ccgggtcccg cgcgtgtac     420 cacatccagg cgggcctacc ggacccgttc cagccccca gctcccgat acggttttac     480 tacgccgtgt ggagcgcgc ctgccgcagc gtgctcctaa cgcaccgtc ggaggccccc     540 cagattgtcc gcggggcctc cgaagacgtc cggaaacaac cctacaacct gaccatcgct     600
tggtttcgga tgggaggcaa ctgtgctatc cccatcacgg tcatggagta caccgaatgc     660
tcctacaaca gtctctgggg gcctgtcccc atccgaacgc agccccgctg gaactactat     720
gacagcttca cgcgccgtcag cgaggataac ctggggttcc tgatgcacgc ccccgcgttt     780
gagaccgccg gcacgtacct gcggctcgtg aagataaacg actggacgga gattacacag     840
tttatcctgg agcaccgagc caagggctcc tgtaagtacg cccttccgct gcgcatcccc     900
ccgtcagcct gcctctcccc ccaggcctac cagcagggg tgacggtgga cagcatcggg     960
```

-continued

| | |
|---|---|
| atgctgcccc gcttcatccc cgagaaccag cgcaccgtcg ccgtatacag cttgaagatc | 1020 |
| gccgggtggc acgggcccaa ggccccatac acgagcaccc tgctgccccc ggagctgtcc | 1080 |
| gagaccccca acgccacgca gccagaactc gccccggaag accccgagga ttcggccctc | 1140 |
| ttggaggacc ccgtggggac ggtggtgccg caaatcccac caaactggca cataccgtcg | 1200 |
| atccaggacg ccgcgacgcc ttaccatccc ccggccaccc cgaacaacat gggcctgatc | 1260 |
| gccggcgcgg tgggcggcag tctcctggta gccctggtca tttgcggaat tgtgtactgg | 1320 |
| atgcgccgcc gcactcaaaa agccccaaag cgcatacgcc tcccccacat ccgggaagac | 1380 |
| gaccagccgt cctcgcacca gcccttgttt tactag | 1416 |

<210> SEQ ID NO 42
<211> LENGTH: 471
<212> TYPE: PRT
<213> ORGANISM: Herpes Simplex Virus-1

<400> SEQUENCE: 42

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Gln Phe Asn Gly Thr Gly Ser Arg Arg Val Tyr His Ile Gln Ala
    130                 135                 140

Gly Leu Pro Asp Pro Phe Gln Pro Pro Ser Leu Pro Ile Thr Val Tyr
145                 150                 155                 160

Tyr Ala Val Leu Glu Arg Ala Cys Arg Ser Val Leu Leu Asn Ala Pro
                165                 170                 175

Ser Glu Ala Pro Gln Ile Val Arg Gly Ala Ser Glu Asp Val Arg Lys
            180                 185                 190

Gln Pro Tyr Asn Leu Thr Ile Ala Trp Phe Arg Met Gly Gly Asn Cys
        195                 200                 205

Ala Ile Pro Ile Thr Val Met Glu Tyr Thr Glu Cys Ser Tyr Asn Lys
    210                 215                 220

Ser Leu Gly Ala Cys Pro Ile Arg Thr Gln Pro Arg Trp Asn Tyr Tyr
225                 230                 235                 240

Asp Ser Phe Ser Ala Val Ser Glu Asp Asn Leu Gly Phe Leu Met His
                245                 250                 255

Ala Pro Ala Phe Glu Thr Ala Gly Thr Tyr Leu Arg Leu Val Lys Ile
            260                 265                 270

Asn Asp Trp Thr Glu Ile Thr Gln Phe Ile Leu Glu His Arg Ala Lys
        275                 280                 285

Gly Ser Cys Lys Tyr Ala Leu Pro Leu Arg Ile Pro Pro Ser Ala Cys

```
                    290                 295                 300
Leu Ser Pro Gln Ala Tyr Gln Gln Gly Val Thr Val Asp Ser Ile Gly
305                 310                 315                 320

Met Leu Pro Arg Phe Ile Pro Glu Asn Gln Arg Thr Val Ala Val Tyr
                325                 330                 335

Ser Leu Lys Ile Ala Gly Trp His Gly Pro Lys Ala Pro Tyr Thr Ser
            340                 345                 350

Thr Leu Leu Pro Pro Glu Leu Ser Glu Thr Pro Asn Ala Thr Gln Pro
        355                 360                 365

Glu Leu Ala Pro Glu Asp Pro Glu Asp Ser Ala Leu Leu Glu Asp Pro
    370                 375                 380

Val Gly Thr Val Val Pro Gln Ile Pro Pro Asn Trp His Ile Pro Ser
385                 390                 395                 400

Ile Gln Asp Ala Ala Thr Pro Tyr His Pro Pro Ala Thr Pro Asn Asn
                405                 410                 415

Met Gly Leu Ile Ala Gly Ala Val Gly Gly Ser Leu Leu Val Ala Leu
            420                 425                 430

Val Ile Cys Gly Ile Val Tyr Trp Met Arg Arg Thr Gln Lys Ala
        435                 440                 445

Pro Lys Arg Ile Arg Leu Pro His Ile Arg Glu Asp Asp Gln Pro Ser
    450                 455                 460

Ser His Gln Pro Leu Phe Tyr
465                 470

<210> SEQ ID NO 43
<211> LENGTH: 1416
<212> TYPE: DNA
<213> ORGANISM: Herpes Simplex Virus-1

<400> SEQUENCE: 43
atggcgcttt tgttgaccac ggtcattgct ctcacttgcc ttggcggctt tgcctcccca      60
ggccctgtgc ctccctctac agccctcagg gagctcattg aggagctggt caacatcacc     120
cagaaccaga aggctccgct ctgcaatggc agcatggtat ggagcatcaa cctgacagct     180
ggcatgtact gtgcagccct ggaatccctg atcaacgtgt caggctgcag tgccatcgag     240
aagacccaga ggatgctgag cggattctgc cgcacaaggt ctcagctggg cagttttcc      300 agcttgcatg tccgagacac caaaatcgag gtggcccagt tgtaaaagga cctgctctta    360
catttaaaga aacttttccg cgagggacag ttcaacggta ccggggtccg cgctcgtac      420 cacatccagg cgggcctacc ggacccgttc cagcccccca gctcccgat acggttttac      480 tacgccgtgt ggagcgcgc ctgccgcagc gtgctcctaa acgcaccgtc ggaggccccc      540
cagattgtcc gcggggcctc cgaagacgtc cggaaacaac cctacaacct gaccatcgct     600
tggtttcgga tgggaggcaa ctgtgctatc cccatcacgg tcatggagta caccgaatgc    660
tcctacaaca gtctctgggg gcctgtccca tccgaacgc agccccgctg gaactactat     720
gacagcttca gcgccgtcag cgaggataac ctggggttcc tgatgcacgc cccgcgtttt    780
gagaccgccg gcacgtacct gcggctcgtg aagataaacg actggacgga gattacacag     840
tttatcctgg agcaccgagc caagggctcc tgtaagtacg cccttccgct gcgcatcccc    900
ccgtcagcct gcctctcccc ccaggcctac cagcagggg tgacggtgga cagcatcggg     960
atgctgcccc gcttcatccc cgagaaccag cgcaccgtcg ccgtatacag cttgaagatc    1020
gccgggtggc acgggcccaa ggcccccatac acgagcaccc tgctgcccc ggagctgtcc    1080
```

```
gagacccca  acgccacgca  gccagaactc  gccccggaag  accccgagga  ttcggccctc    1140
ttggaggacc  ccgtggggac  ggtggtgccg  caaatcccac  caaactggca  cataccgtcg    1200
atccaggacg  ccgcgacgcc  ttaccatccc  ccggccaccc  cgaacaacat  gggcctgatc    1260
gccggcgcgg  tgggcggcag  tctcctggta  gccctggtca  tttgcggaat  tgtgtactgg    1320
atgcgccgcc  gcactcaaaa  agccccaaag  cgcatacgcc  tcccccacat  ccgggaagac    1380
gaccagccgt  cctcgcacca  gcccttgttt  tactag                                1416
```

```
<210> SEQ ID NO 44
<211> LENGTH: 471
<212> TYPE: PRT
<213> ORGANISM: Herpes Simplex Virus-1

<400> SEQUENCE: 44
```

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Gln Phe Asn Gly Thr Gly Val Arg Arg Ser Tyr His Ile Gln Ala
    130                 135                 140

Gly Leu Pro Asp Pro Phe Gln Pro Pro Ser Leu Pro Ile Thr Val Tyr
145                 150                 155                 160

Tyr Ala Val Leu Glu Arg Ala Cys Arg Ser Val Leu Leu Asn Ala Pro
                165                 170                 175

Ser Glu Ala Pro Gln Ile Val Arg Gly Ala Ser Glu Asp Val Arg Lys
            180                 185                 190

Gln Pro Tyr Asn Leu Thr Ile Ala Trp Phe Arg Met Gly Gly Asn Cys
        195                 200                 205

Ala Ile Pro Ile Thr Val Met Glu Tyr Thr Glu Cys Ser Tyr Asn Lys
    210                 215                 220

Ser Leu Gly Ala Cys Pro Ile Arg Thr Gln Pro Arg Trp Asn Tyr Tyr
225                 230                 235                 240

Asp Ser Phe Ser Ala Val Ser Glu Asp Asn Leu Gly Phe Leu Met His
                245                 250                 255

Ala Pro Ala Phe Glu Thr Ala Gly Thr Tyr Leu Arg Leu Val Lys Ile
            260                 265                 270

Asn Asp Trp Thr Glu Ile Thr Gln Phe Ile Leu Glu His Arg Ala Lys
        275                 280                 285

Gly Ser Cys Lys Tyr Ala Leu Pro Leu Arg Ile Pro Pro Ser Ala Cys
    290                 295                 300

Leu Ser Pro Gln Ala Tyr Gln Gln Gly Val Thr Val Asp Ser Ile Gly
305                 310                 315                 320

```
Met Leu Pro Arg Phe Ile Pro Glu Asn Gln Arg Thr Val Ala Val Tyr
            325             330             335

Ser Leu Lys Ile Ala Gly Trp His Gly Pro Lys Ala Pro Tyr Thr Ser
            340             345             350

Thr Leu Leu Pro Pro Glu Leu Ser Glu Thr Pro Asn Ala Thr Gln Pro
        355             360             365

Glu Leu Ala Pro Glu Asp Pro Glu Asp Ser Ala Leu Leu Glu Asp Pro
        370             375             380

Val Gly Thr Val Val Pro Gln Ile Pro Pro Asn Trp His Ile Pro Ser
385             390             395             400

Ile Gln Asp Ala Ala Thr Pro Tyr His Pro Pro Ala Thr Pro Asn Asn
            405             410             415

Met Gly Leu Ile Ala Gly Ala Val Gly Gly Ser Leu Leu Val Ala Leu
            420             425             430

Val Ile Cys Gly Ile Val Tyr Trp Met Arg Arg Thr Gln Lys Ala
            435             440             445

Pro Lys Arg Ile Arg Leu Pro His Ile Arg Glu Asp Asp Gln Pro Ser
        450             455             460

Ser His Gln Pro Leu Phe Tyr
465             470
```